US012648792B2

(12) United States Patent
Konh et al.

(10) Patent No.: US 12,648,792 B2
(45) Date of Patent: Jun. 9, 2026

(54) MRI COMPATIBLE STEERABLE SURGICAL APPARATUS AND METHOD

(71) Applicant: University of Hawaii, Honolulu, HI (US)

(72) Inventors: Bardia Konh, Honolulu, HI (US); Blayton Padasdao, Honolulu, HI (US); Samuel Lafreniere, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 53 days.

(21) Appl. No.: 18/629,447

(22) Filed: Apr. 8, 2024

(65) Prior Publication Data

US 2024/0341802 A1      Oct. 17, 2024

Related U.S. Application Data

(60) Provisional application No. 63/460,012, filed on Apr. 17, 2023.

(51) Int. Cl.
A61B 17/34      (2006.01)
A61B 5/055      (2006.01)
            (Continued)

(52) U.S. Cl.
CPC .......... A61B 17/3403 (2013.01); A61B 5/055 (2013.01); A61B 10/0233 (2013.01); (Continued)

(58) Field of Classification Search
CPC ............ A61B 10/0233; A61B 17/3403; A61B 17/3476; A61B 2010/0208; A61B 2017/00017; A61B 2017/00309; A61B 2017/00327; A61B 2017/00398; A61B 2017/00402; A61B 2034/2051; (Continued)

(56) References Cited

U.S. PATENT DOCUMENTS

2022/0133354 A1      5/2022  Konh
2023/0277192 A1*     9/2023  Constandinou .... A61B 17/1227
                                                         606/142

OTHER PUBLICATIONS

Addicott, B. et al., "Direct magnetic resonance imaging-guided biopsy of the prostate: lessons learned in establishing a regional referral center," Translational Andrology and Urology, vol. 6, No. 3, Jun. 2017, pp. 395-405.

(Continued)

*Primary Examiner* — Michael T Rozanski
(74) *Attorney, Agent, or Firm* — Withrow & Terranova, PLLC; Vincent K. Gustafson

(57)      ABSTRACT

A steerable surgical apparatus comprises a steerable surgical tubular needle, a needle manipulation apparatus with multiple actuators (permitting adjustment of needle rotation, translation, and bending), fiducial markers affixed to the needle manipulation apparatus, encoders configured to sense movements initiated by actuators, and a control unit. The needle manipulation apparatus is devoid of ferrous materials, and is configured to be placed and operated within an MRI machine bore. The control unit determines position and orientation for: (i) the needle manipulation apparatus relative to the MRI machine bore, such as by MRI imaging of the fiducial markers, and (ii) the needle inserted into a patient within the MRI machine bore, such as by kinematics utilizing signals of the encoders.

20 Claims, 28 Drawing Sheets

(51) Int. Cl.

| | |
|---|---|
| *A61B 10/02* | (2006.01) |
| *A61B 17/00* | (2006.01) |
| *A61M 25/09* | (2006.01) |
| *A61N 5/10* | (2006.01) |

(52) U.S. Cl.
CPC ... *A61B 17/3476* (2013.01); *A61M 25/09041* (2013.01); *A61N 5/1007* (2013.01); *A61B 2010/0208* (2013.01); *A61B 2017/00402* (2013.01)

(58) Field of Classification Search
CPC ...... A61B 2034/2059; A61B 2034/301; A61B 2090/374; A61B 2090/3954; A61B 34/30; A61M 25/09041; A61N 5/1007
See application file for complete search history.

(56) References Cited

OTHER PUBLICATIONS

Ahdoot, M. et al., "MRI-Targeted, Systematic, and Combined Biopsy for Prostate Cancer Diagnosis," New England Journal of Medicine, vol. 382, No. 10, Mar. 2020, pp. 917-928.

Karimi, S. et al., "Self-Sensing Electrical Resistance Feedback Control of Multiple Interacting SMA Actuators in a 3D Steerable Active Needle," Journal of Intelligent Material Systems and Structures, vol. 31, No. 12, Jun. 2020, pp. 1524-1540.

Kasivisvanathan, V. et al., "Magnetic Resonance Imaging-Targeted Biopsy Versus Systematic Biopsy in the Detection of Prostate Cancer: A Systematic Review and Meta-Analysis," European Urology, vol. 76, Issue 3, Sep. 2019, pp. 284-303.

Konh, B. et al., "Integrating Robot-Assisted Ultrasound Tracking and 3D Needle Shape Prediction for Real-Time Tracking of the Needle Tip in Needle Steering Procedures," International Journal of Medical Robotics and Computer Assisted Surgery, vol. 17, No. 3, May 2021, John Wiley & Sons Ltd., 14 pages.

Konh, B. et al., "Steering a Tendon-Driven Needle in High-Dose-Rate Prostate Brachytherapy for Patients with Pubic Arch Interference," 2021 International Symposium on Medical Robotics (ISMR), Nov. 2021, 17 pages.

Meermeier, N. et al., "Impact of Direct MRI-Guided Biopsy of the Prostate on Clinical Management," American Journal of Roentgenology, vol. 213, No. 2, Aug. 2019, pp. 371-376.

Padasdao, B. et al., "Modeling and Operator Control of a Robotic Tool for Bidirectional Manipulation in Targeted Prostate Biopsy," 2022 International Symposium on Medical Robotics (ISMR), Apr. 2022, 16 pages.

Padasdao, B. et al., "Shape Memory Alloy Actuators in an Active Needle Modeling , Precise Assembly, and Performance Evaluation," Journal of Manufacturing Science and Engineering, vol. 143, No. 2, Jul. 2020, 10 pages.

Padasdao, B. et al., "Teleoperated and Automated Control of a Robotic Tool for Targeted Prostate Biopsy," Journal of Medical Robotics Research, vol. 8, Jan. 2023, 25 pages.

Perrin, A. et al., "The Utility of In-Bore Multiparametric Magnetic Resonance-Guided Biopsy in Men with Negative Multiparametric Magnetic Resonance-Ultrasound Software-Based Fusion Targeted Biopsy," Urologic Oncology: Seminars and Original Investigations, vol. 39, Issue 5, May 2021, pp. 297.e9-297.e16.

Philips, "Philips DynaTRIM Targeted Trans-Rectal Interventional MRI," available as early as Apr. 2023 from the Internet: [URL: https://www.philips.co.in/healthcare/product/HC784008/dynatrim-targeted-trans-rectal-interventional-mri], 3 pages.

Philips, "Targeted prostate biopsy guidance with DynaTRIM," Apr. 2020, Koninklijke Philips N.V., 2 pages.

Scali, M., et al., "Needle-like Instruments for Steering through Solid Organs: A Review of the Scientific and Patent Literature," Proceedings of the Institution of Mechanical Engineers Part H Journal of Engineering in Medicine, Dec. 2016, pp. 250-265.

Su, H. et al., "Real-Time MRI-Guided Needle Placement Robot with Integrated Fiber Optic Force Sensing," Proceedings—IEEE International Conference on Robotics and Automation, May 2011, IEEE, pp. 1583-1588.

Van De Berg, N. J., et al., "Design Choices in Needle Steering—A Review," IEEE/ASME Transactions on Mechatronics, vol. 20, Issue 5, Oct. 2015, IEEE, pp. 2172-2183.

Van Der Leest, M. et al., "Head-to-head Comparison of Transrectal Ultrasound-guided Prostate Biopsy Versus Multiparametric Prostate Resonance Imaging with Subsequent Magnetic Resonance-guided Biopsy in Biopsy-naïve Men with Elevated Prostate-specific Antigen: A Large Prospective Multicenter Clinical Study," European Urology, vol. 75, Issue 4, Apr. 2019, Elsevier, pp. 570-578.

Varnamkhasti, Z.K. et al., "Compact 3D-Printed Active Flexible Needle for Percutaneous Procedures," Surgical Innovation, vol. 27, No. 4, Aug. 2020, pp. 402-405.

Varnamkhasti, Z.K. et al., "Design, Fabrication, and Testing of a Flexible Three-Dimensional Printed Percutaneous Needle with Embedded Actuators," ASME Journal of Medical Devices, vol. 15, No. 2, Dec. 2020, 10 pages.

* cited by examiner

65

1

MRI COMPATIBLE STEERABLE SURGICAL APPARATUS AND METHOD

CROSS-REFERENCE TO RELATED APPLICATION(S)

This application claims priority to U.S. Provisional Patent Application No. 63/460,012 filed on Apr. 17, 2023, wherein the entire disclosure of the foregoing application is hereby incorporated by reference herein.

GOVERNMENT RIGHTS IN INVENTION

This invention was made with government support under K25 EB030562 awarded by the National Institutes of Health. The government has certain rights in the invention.

TECHNICAL FIELD

This disclosure relates to steerable surgical apparatuses for controlling steerable needles that are insertable in tissues of mammalian bodies, as well as methods for use of such apparatuses.

BACKGROUND

Surgical needles are commonly used in percutaneous diagnostic and therapeutic procedures. These procedures include tissue removal (biopsy), internal radiotherapy (brachytherapy), thermal ablations, and targeted drug delivery. The success of these procedures highly depends on the accuracy of needle placement at target locations. For example, malposition of the biopsy needle could result in a false diagnosis. Similarly, in brachytherapy, inaccurate positioning of the radioactive seeds could cause damage to the healthy tissue instead of attacking the cancerous cells. Precise delivery of therapeutic drugs to the diseased tissue or taking biopsy samples from suspicious tissue for diagnosis procedures is the most important factor governing the success of needle-based procedures.

Insertion of a narrow tubular body such as a flexible needle into a patient for performing a subcutaneous surgical procedure is a complex procedure for a physician. Typically, a surgeon will guide a needle to a target using an ultrasound image, which is susceptible to image noise, and it is frequently difficult to distinguish the needle from surrounding tissue unless there is precise alignment between the needle and an ultrasound probe.

Image-guided biopsy is known as a popular and effective diagnosis procedure for the detection of many different types of cancers, including prostate cancer. For prostate cancer, transrectal ultrasound (TRUS) guided core needle biopsies are in common practice; however, these types of biopsies have a poor cancer detection rate (e.g., on the order of 26%).

Magnetic resonance imaging (MRI) can volumetrically image the human body in a non-invasive manner without the use of ionizing radiation. However, the closed-bore nature of these systems limits surgical access to a patient during imaging. MRI fusion prostate biopsy is a newer technique that combines MRI images with ultrasound (US) images in real time and performed under US guidance. This technique is widely practiced throughout the nation, either transperineally or transrectally. Transrectal prostate biopsy is the method currently preferred by most institutes because of its shorter procedure time, despite its higher risk of bleeding and infection.

Current practices for prostate biopsy, e.g., systematic 12-core biopsy or the MRI-US fusion method, are associated with a high volume of misdiagnoses, as well as instances of under- and over-diagnosis. Recent strides in medical robotics offer promising solutions, aiming to enhance precision and efficiency in diagnostics. Integrating multiparametric MRI (mpMRI) into this landscape has improved tumor visualization. However, in-bore MRI prostate biopsy adoption is hindered by cost constraints and procedural time issues, and the use of robotic systems is complicated by the inherent incompatibility between traditional electromagnetic servomotor actuators commonly used in commercial medical robots. Current passive devices in use (e.g., Philips, DynaTRIM; Invivo Corp [1]) lack crucial in-bore needle actuation, leading to extended procedural times and potential impacts on diagnostic accuracy. Additionally, proposed robotic systems that are in the research stage lack proper needle steering in a curved trajectory for accurate targeted prostate biopsy.

Studies done in 2019 [2,3] and 2020 [4] have shown that targeted biopsy performed under magnetic resonance imaging (MRI) results in higher detection rates of more malignant lesions with fewer cores, and thus reducing the number of unnecessary biopsies. A more recent study in 2021 on 53 men showed that in-bore prostate biopsy was able to detect significant prostate cancer in one in four patients with previous negative fusion biopsy [1]. Another study on 127 patients [6] demonstrated association of direct MRI-guided biopsy with high rates of significant prostate cancer detection and subsequent definitive treatment across common clinical scenarios [7]. Despite the higher success in prostate cancer detection, MRI-guided biopsies are offered only to specific patients at few institutes around the nation.

High-dose-rate (HDR) brachytherapy (BT), which entails delivery of temporary high-dose radiation to the prostate gland to irradiate cancer cells, has been identified as one of the most effective treatment modalities. Low-dose-rate (LDR) BT involves implantation of permanent radioactive seeds. Conventional rigid needles and templates only allow insertions for BT typically in a straight trajectory, with no conformity to the patient's specific anatomy. Active steerable needles introduce the potential to add clinical value to needle-based interventions by correcting natural or unintended curvatures, correct deviations from desired straight trajectories, or enabling deliberately planned curved trajectories. Sub-optimal catheter implantation may contribute to insufficient dose to the cancer and/or inadvertent radiation of the organs at risk.

Although systems with steerable surgical needles utilizing transverse ultrasound probe images in combination with saved and predicted needle tip information are known (such as disclosed in U.S. Patent Application Publication No. 2022/0133354 A1 to Konh), such systems are not useable with MRI machines. Need exists for improved targeting accuracy for procedures utilizing steerable surgical needles, including but not limited to, biopsy, HDR brachytherapy, LDR brachytherapy, and targeted delivery of therapeutic agents.

SUMMARY

This disclosure relates to steerable surgical apparatuses for controlling steerable tubular needles that are insertable in tissues of mammalian bodies, as well as methods for using such apparatuses. A needle manipulation apparatus is devoid of ferrous materials and is configured to be placed and operated within a magnetic resonance imaging (MRI)

machine bore, thereby compensating for limited access by physicians to patients positioned within closed-bore MRI machines. The needle manipulation apparatus includes actuators configured to permit adjustment of needle rotation, needle translation, and needle bending, and fiducial markers and encoders are associated with the needle manipulation apparatus. A control unit determines position and orientation for: (i) the needle manipulation apparatus relative to the MRI machine bore (e.g., utilizing information derived from MRI imaging of the fiducial markers), and (ii) the steerable surgical needle inserted into a body of a patient within the MRI machine bore (e.g., by kinematics utilizing signals of the encoders). The control unit may additionally be used to control operation of the actuators to effectuate adjustment of needle rotation, needle translation, and needle bending when the needle is inserted into the patient within the magnetic resonance imaging machine bore. A method for performing a surgical procedure utilizing the steerable surgical apparatus includes determining position and orientation for items (i) and (ii) above, and controlling the actuators to adjust needle rotation, needle translation, and needle bending of the steerable surgical tubular needle and thereby control movement of the steerable surgical tubular needle within the body of the patient, while the needle manipulation apparatus as well as the patient are within the MRI machine bore.

In one aspect, the disclosure relates to a steerable surgical apparatus that comprises: a steerable surgical tubular needle, a needle manipulation apparatus comprising a plurality of controllable actuators, a plurality of fiducial markers affixed to the needle manipulation apparatus, a plurality of encoders configured to sense movements initiated by the plurality of controllable actuators, and a control unit. The needle manipulation apparatus is configured to manipulate the steerable surgical tubular needle. The plurality of controllable actuators is configured to permit adjustment of needle rotation, needle translation, and needle bending. The needle manipulation apparatus is devoid of ferrous materials, and is configured to be placed and operated within a magnetic resonance imaging machine bore. The control unit is configured to: (i) utilize positional information derived from imaging the plurality of fiducial markers to establish position and orientation of the needle manipulation apparatus within the magnetic resonance imaging machine bore, and (ii) utilize signals obtained from the plurality of encoders to determine position and orientation of the steerable surgical tubular needle when inserted into a body of a patient within the magnetic resonance imaging machine bore.

In certain embodiments, the control unit is further configured to control operation of the plurality of controllable actuators to effectuate adjustment of needle rotation, needle translation, and needle bending when the needle is inserted into the patient within the magnetic resonance imaging machine bore.

In certain embodiments, the plurality of controllable actuators comprises nonmagnetic piezoelectric actuators.

In certain embodiments, the control unit is configured to apply kinematic functions in combination with the signals obtained from the plurality of encoders to determine position and orientation of the steerable surgical tubular needle when inserted into a patient within the magnetic resonance imaging machine bore.

In certain embodiments, the steerable surgical apparatus further comprises first and second tendons extending through an interior of the steerable surgical tubular needle, wherein: the steerable surgical tubular needle comprises a tip portion; and the plurality of controllable actuators comprises a first nonmagnetic piezoelectric actuator configured to selectively apply tension to the first tendon for bending the tip portion in a first direction, and comprises a second nonmagnetic piezoelectric actuator configured to selectively apply tension to the second tendon for bending the tip portion in a second direction.

In certain embodiments, the steerable surgical tubular needle comprises multiple groups of transverse notches defined in a wall of the tubular needle, wherein each group of transverse notches of the multiple groups of transverse notches extends in a different direction relative to each other group of transverse notches.

In certain embodiments, the steerable surgical tubular needle comprises: a tubular body having a distal end; a longitudinal passage extending in a longitudinal direction within an interior of the steerable surgical tubular needle; a moveable tray member arranged at the distal end of the tubular body and coupled to a longitudinal guidewire, the moveable tray member comprising at least one lateral opening in communication with the longitudinal passage, and being configured to translate in the longitudinal direction between an extended position and a retracted position; and a retractable tip member positionable at a distal end of the moveable tray member.

In certain embodiments, the steerable surgical apparatus further comprises a tray member actuator configured to manipulate the guidewire to translate the moveable tray member in the longitudinal direction.

In certain embodiments, the steerable surgical apparatus further comprises a fiducial frame containing the plurality of fiducial markers, wherein multiple different fiducial markers of the plurality of fiducial markers are supported by the fiducial frame to be positioned in different respective planes, wherein each fiducial marker of the plurality of fiducial markers contains MRI-visible high contrast fluid.

In certain embodiments, the plurality of controllable actuators comprises a third actuator configured to permit adjustment of needle translation, and the control unit is configured to control operation of the third actuator.

In certain embodiments, the plurality of controllable actuators comprises a fourth actuator configured to permit adjustment of needle rotation, and the control unit is configured to control operation of the fourth actuator.

In certain embodiments, the steerable surgical apparatus further comprises at least one translation mechanism configured to permit translation of the needle manipulation apparatus along at least one axis, and at least one translation mechanism actuator to control translation of the needle manipulation apparatus along the at least one axis.

In certain embodiments, the at least one axis comprises a plurality of orthogonal axes.

In certain embodiments, the control unit is configured to control operation of the at least one translation mechanism actuator.

In certain embodiments, the at least one translation mechanism comprises at least one Scott-Russell mechanism.

In another aspect, the disclosure relates to a method for performing a surgical procedure utilizing a steerable surgical apparatus as disclosed herein (e.g., including a steerable surgical tubular needle, a needle manipulation apparatus comprising a plurality of controllable actuators, a plurality of fiducial markers affixed to the needle manipulation apparatus, a plurality of encoders configured to sense movements initiated by the plurality of controllable actuators, and a control unit) in conjunction with a magnetic resonance imaging device having a magnetic resonance imaging machine bore. The method comprises: inserting a steerable surgical tubular needle into a body of a patient; and, while the patient and the needle manipulation apparatus are present within the magnetic resonance imaging bore, performing the following items (a) to (c): (a) supplying positional information derived from imaging of the fiducial markers to the control unit, and utilizing, by the control unit, the positional information to establish position and orientation of the needle manipulation apparatus; (b) utilizing, by the control unit, signals obtained from the plurality of encoders to determine position and orientation of the steerable surgical tubular needle within the body of the patient; and (c) controlling, by the control unit, the plurality of controllable actuators to adjust needle rotation, needle translation, and needle bending of the steerable surgical tubular needle and thereby control movement of the steerable surgical tubular needle within the body of the patient.

In certain embodiments, the steerable surgical apparatus comprises first and second tendons extending through an interior of the steerable surgical tubular needle, the steerable surgical tubular needle comprises a tip portion, the plurality of controllable actuators comprises a first and second non-magnetic piezoelectric actuators; and the controlling, by the control unit, of the plurality of controllable actuators comprises controlling the first nonmagnetic piezoelectric actuator to selectively apply tension to the first tendon for bending the tip portion in a first direction, and comprises controlling the second nonmagnetic piezoelectric actuator to selectively apply tension to the second tendon for bending the tip portion in a second direction.

In certain embodiments, the steerable surgical tubular needle comprises a tubular body having a distal end; a longitudinal passage extending in a longitudinal direction within an interior of the steerable surgical tubular needle; a moveable tray member arranged at the distal end of the tubular body and coupled to a longitudinal guidewire, the moveable tray member comprising at least one lateral opening in communication with the longitudinal passage, and being configured to translate in the longitudinal direction between an extended position and a retracted position; and a retractable tip member positionable at a distal end of the moveable tray member. In such an embodiment, the method further comprises controlling, by the control unit, a tray member actuator coupled with the guidewire to translate the moveable tray member through the longitudinal passage.

In certain embodiments, the method further comprises receiving a tissue sample from the patient through the at least one lateral opening into the moveable tray member, and removing the tissue sample by translating the moveable tray member through the longitudinal passage.

In certain embodiments, the method further comprises receiving image data from the magnetic resonance imaging device; and responsive to receipt of the image data, controlling, by the control unit, the plurality of controllable actuators to adjust needle rotation, needle translation, and needle bending of the steerable surgical tubular needle and thereby control movement of the steerable surgical tubular needle within the body of the patient.

In certain embodiments, the surgical procedure comprises brachytherapy, and the method further comprises delivering at least one radioactive material through the steerable surgical needle to one or more locations within the body of the patient.

In another aspect, the disclosure relates to a steerable surgical apparatus comprising: a steerable surgical tubular needle; a needle manipulation apparatus configured to manipulate the steerable surgical tubular needle, the needle manipulation apparatus comprising a plurality of controllable actuators configured to permit adjustment of needle rotation, needle translation, and needle bending, wherein the needle manipulation apparatus is devoid of ferrous materials, and the needle manipulation apparatus is configured to be placed and operated within a magnetic resonance imaging machine bore; and a control unit configured to control operation of the plurality of controllable actuators to effectuate adjustment of needle rotation, needle translation, and needle bending when the needle is inserted into the patient within the magnetic resonance imaging machine bore.

In certain embodiments, the steerable surgical apparatus further comprises first and second tendons extending through an interior of the steerable surgical tubular needle, wherein: the steerable surgical tubular needle comprises a tip portion; and the plurality of controllable actuators comprises a first nonmagnetic piezoelectric actuator configured to selectively apply tension to the first tendon for bending the tip portion in a first direction, and comprises a second nonmagnetic piezoelectric actuator configured to selectively apply tension to the second tendon for bending the tip portion in a second direction.

In certain embodiments, the steerable surgical tubular needle comprises multiple groups of transverse notches defined in a wall of the tubular needle, wherein each group of transverse notches of the multiple groups of transverse notches extends in a different direction relative to each other group of transverse notches.

In certain embodiments, the plurality of controllable actuators comprises a third actuator configured to permit adjustment of needle translation and a fourth actuator configured to permit adjustment of needle rotation, and the control unit is configured to control operation of the third actuator and the fourth actuator.

In another aspect, any two or more features of aspects and/or embodiments disclosed herein may be combined for additional advantage.

DETAILED DESCRIPTION

This disclosure relates to steerable surgical apparatuses for controlling steerable tubular needles that are insertable in tissues of mammalian bodies, as well as methods for using such apparatuses for performing surgical procedures (including, but not limited to, biopsy, brachytherapy, targeted delivery of therapeutic agents, and the like), with such apparatuses and methods being compatible for use in MRI machines. Exemplary steerable tubular needles are disclosed in U.S. Patent Application Publication No. 2022/0133354

A1, now U.S. Pat. No. 12,402,913, to Konh, which is incorporated by reference herein. Steerable tubular needles disclosed herein may include a tubular body (e.g., of nitinol) having compliant flexure section that enables multi-directional bending via actuation using multiple internal tendons extending within an interior of the tubular needle and coupled with a needle manipulation apparatus. The tendons are independently actuatable (e.g., using actuators arranged external to the needle) to cause the compliant flexure section to bend. Further actuators may be used to advance (i.e., translate) and rotate the needle. In combination, controlling advancement, rotation, and bending of the needle permits trajectory of the needle through tissue to be controlled. The actuators and other components (e.g., sensors, mechanisms, structural items, and the like) of a steerable surgical system are devoid of ferrous materials and configured to be placed and operated within an MRI machine bore, thereby compensating for limited access by physicians to patients positioned within closed-bore MRI machines, while overcoming challenges with incompatibility between conventional electromagnetic motors and the strong magnetic fields present in such an environment.

Figure 1:
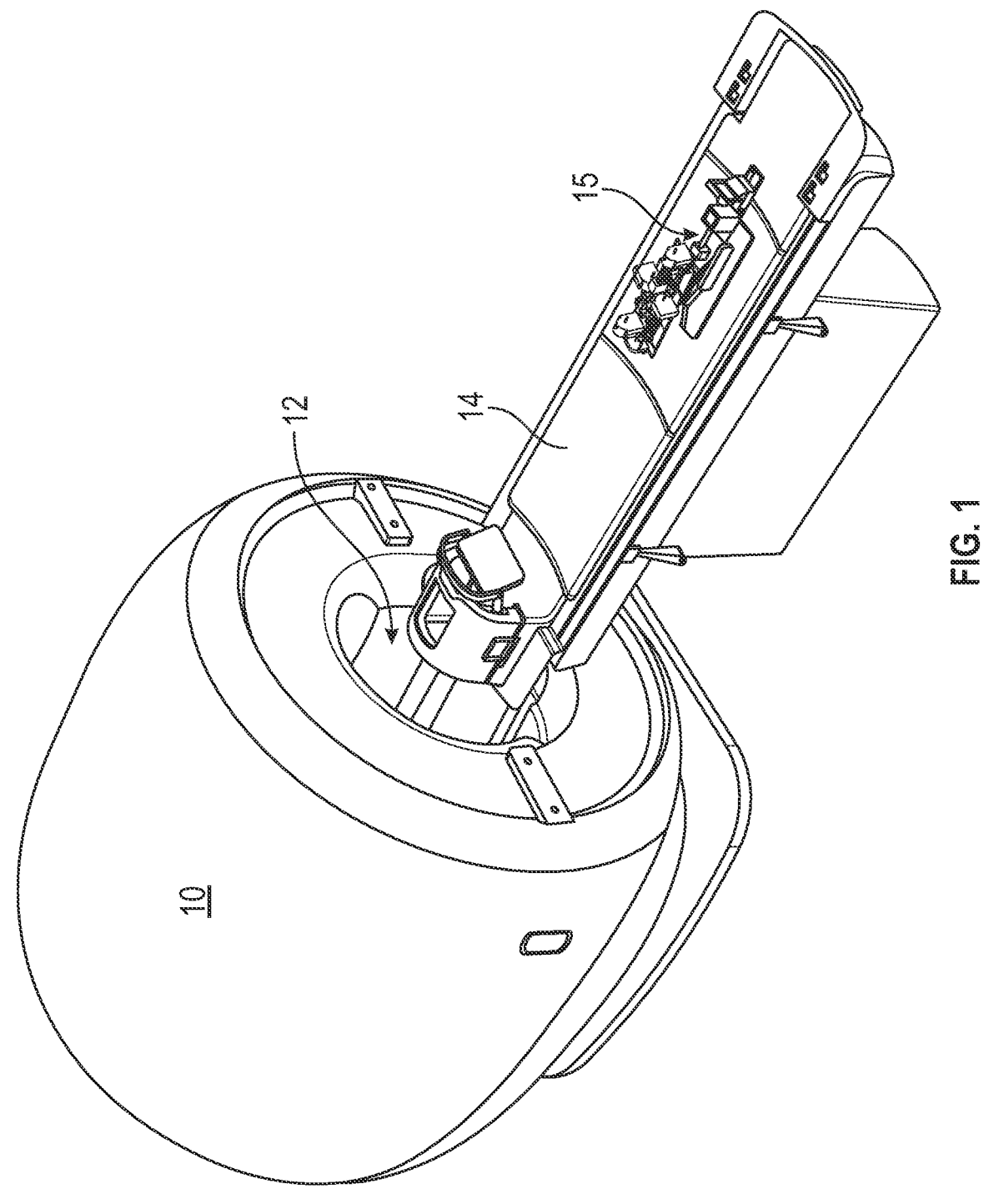
FIG. 1 is a perspective view of a magnetic resonance imaging (MRI) machine having a bore, with a slidable table configured to receive a patient being positioned outside the MRI machine bore, and with a steerable surgical apparatus according to one embodiment of the present disclosure positioned on the slidable table.

FIG. 1 is a perspective view of an MRI machine 10 having a bore 12, with a slidable table 14 configured to receive a patient (not shown) being positioned outside the MRI machine bore 12, and with a steerable surgical apparatus 15 according to one embodiment being positioned on the slidable table 14. Although a patient is not shown in FIG. 1, it is to be appreciated that a patient may be supporting in a lying (e.g., supine, prone, or semilithotomy) position on the slidable table 14, and the steerable surgical apparatus 15 may be positioned proximate to the patient to permit a steerable surgical tubular needle to be inserted into the body of the patient as part of performing a surgical procedure.

A steerable surgical apparatus as disclosed herein includes: a steerable surgical tubular needle; a needle manipulation apparatus configured to manipulate the steerable surgical tubular needle, the needle manipulation apparatus comprising a plurality of controllable actuators configured to permit adjustment of needle rotation, needle translation (e.g., advancement or retraction relative to the body of a patient), and needle bending, wherein the needle manipulation apparatus is devoid of ferrous and magnetic materials and is configured to be placed and operated within a magnetic resonance imaging machine bore. In certain embodiments, a steerable surgical apparatus may include additional mechanisms to permit a needle manipulation apparatus to be moved along one or more additional axes (e.g., in a longitudinal horizontal direction, a lateral horizontal direction, and/or a vertical direction). In certain embodiments, one additional mechanism, some additional mechanisms, or all additional mechanisms may be automatically controlled (e.g., using MRI-compatible actuators), or may be manually repositioned. Before describing needle manipulation apparatuses according to various embodiments, mechanisms permitting a needle manipulation apparatus to be moved along one or more additional axes will be introduced in FIGS. 2A and 2B.

Figure 2A:
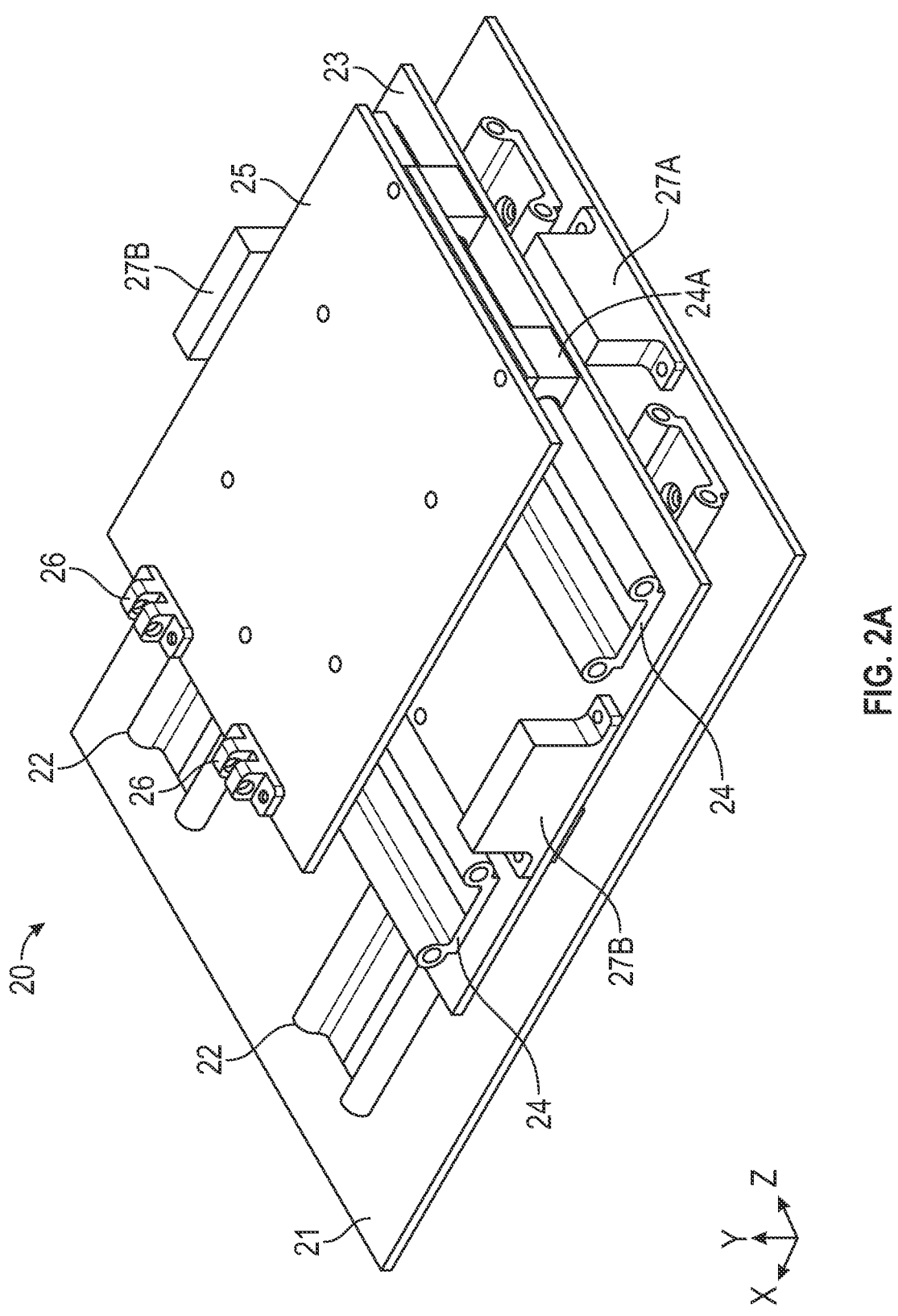
FIG. 2A is a perspective view of a two-axis horizontal positioning stage that may be used with a steerable surgical apparatus according to one or more embodiments of the present disclosure.

FIG. 2A is a perspective view of a two-axis horizontal positioning stage 20 that may be used with a steerable surgical apparatus according to one or more embodiments of the present disclosure. The horizontal positioning stage 20 includes a lower gantry plate 21, and intermediate gantry plate 23, and an upper gantry plate 25. The lower gantry plate 21 includes two x-direction gantry rails 22 extending in an x-direction (e.g., longitudinal horizontal direction), and the intermediate gantry plate 23 includes two z-direction gantry rails 24 extending in a z-direction (e.g., lateral horizontal direction). First carriage members (not shown) on an underside of the intermediate gantry plate 23 are configured to cooperate with the x-direction gantry rails 22 to permit the intermediate gantry plate 23 to slide in the x-direction relative to the lower gantry plate 21, while second carriage members (not shown) on an underside of the upper gantry plate 25 are configured to cooperate with the y-direction gantry rails 24 to permit the upper gantry plate 25 to slide in the z-direction relative to the intermediate gantry plate 23. A first stop plate 27A protruding upward from the lower gantry plate 21 limits excess travel of the intermediate gantry plate 23 in the x-direction, while second stop plates 27B protruding upward from the intermediate gantry plate 23 limit excess travel of the upper gantry plate 25 in the z-direction. The upper gantry plate 25 includes pivot mounts 26 for receiving forward links (31 in FIG. 2B) of a vertical positioning stage (30 in FIG. 2B). As shown, the two-axis horizontal positioning stage 20 is devoid of any actuators configured to move the intermediate gantry plate 23 or the upper gantry plate 25. However, in certain embodiments, one or more actuators may be provided to effectuate movement of the intermediate gantry plate 23 in the z-direction and/or movement of the upper gantry plate 25 in the x-direction. Each component of the horizontal positioning stage 20 is devoid of ferrous materials. For example, materials, such as aluminum, acrylic, and various polymers may be used.

Figure 2B:
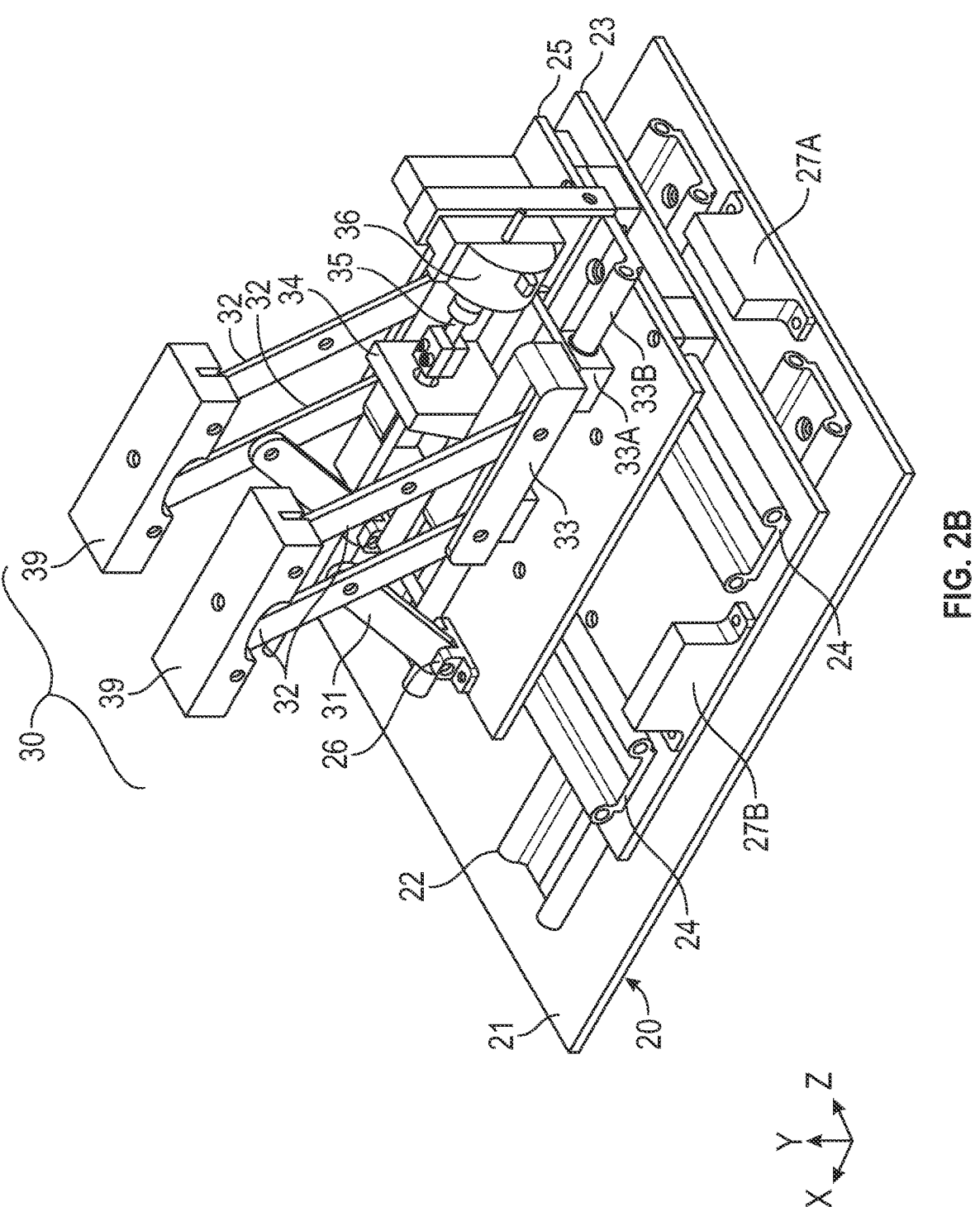
FIG. 2B is a perspective view of the two-axis horizontal positioning stage of FIG. 2A, with a vertical positioning stage comprising a Scott-Russell mechanism and a rotary actuator positioned atop the horizontal positioning stage to form a three-axis positioning stage configured to be operated within a bore of an MRI machine.

FIG. 2B is a perspective view of the two-axis horizontal positioning stage 20 of FIG. 2A, in combination with a vertical positioning stage 30 comprising a Scott-Russell mechanism (including forward link 31, parallel links 32, traveling linkage 33, carriage members 33A, x-axis rail 33B, and pusher 34) as well as a piezoelectric rotary actuator 36 positioned atop the upper gantry plate 25 of the horizontal positioning stage 20 to form (in combination) a three-axis positioning stage configured to be operated within a bore of an MRI machine. The vertical positional stage 30 includes a threadless lead screw mechanism 35 arranged between the piezoelectric rotary actuator 36 and the pusher 34. The pusher 34 is coupled to the traveling linkage 33, with the carriage members 33A arranged along an underside of the traveling linkage 33 being configured to move along the x-axis rail 33B in order to permit movement of the traveling linkage 33 along the x-direction. Upper mounts 39 are pivotally mounted to upper ends of the parallel links 32 to enable mounting and provide support to a needle manipulation apparatus (e.g., 40 in FIG. 2C). The forward link 31 is pivotally coupled between pivot mounts 26 of the upper gantry plate 25 and leading ones of the parallel links 32. In use, rotation of the piezoelectric rotary actuator 36 and the threadless lead screw mechanism 35 causes movement of the pusher 34 that is coupled to the traveling linkage 33. Movement of the traveling linkage 33, to which the parallel links 32 are pivotally coupled, causes pivotal movement of the parallel links 32, thereby causing the upper mounts 39 to rise or fall in the y-direction. Such movement permits vertical positional adjustment of the upper mounts 39, and vertical positional adjustment of a needle manipulation apparatus (e.g., 40 in FIG. 2C) when supported by the upper mounts 39. Each component of the vertical positioning stage 30 is devoid of ferrous materials. In certain embodiments, the horizontal positioning stage 20 may be manually positioned, while the positioning of the vertical positioning stage 30 (and an associated needle manipulation apparatus) may be controlled with actuators.

Figure 2C:
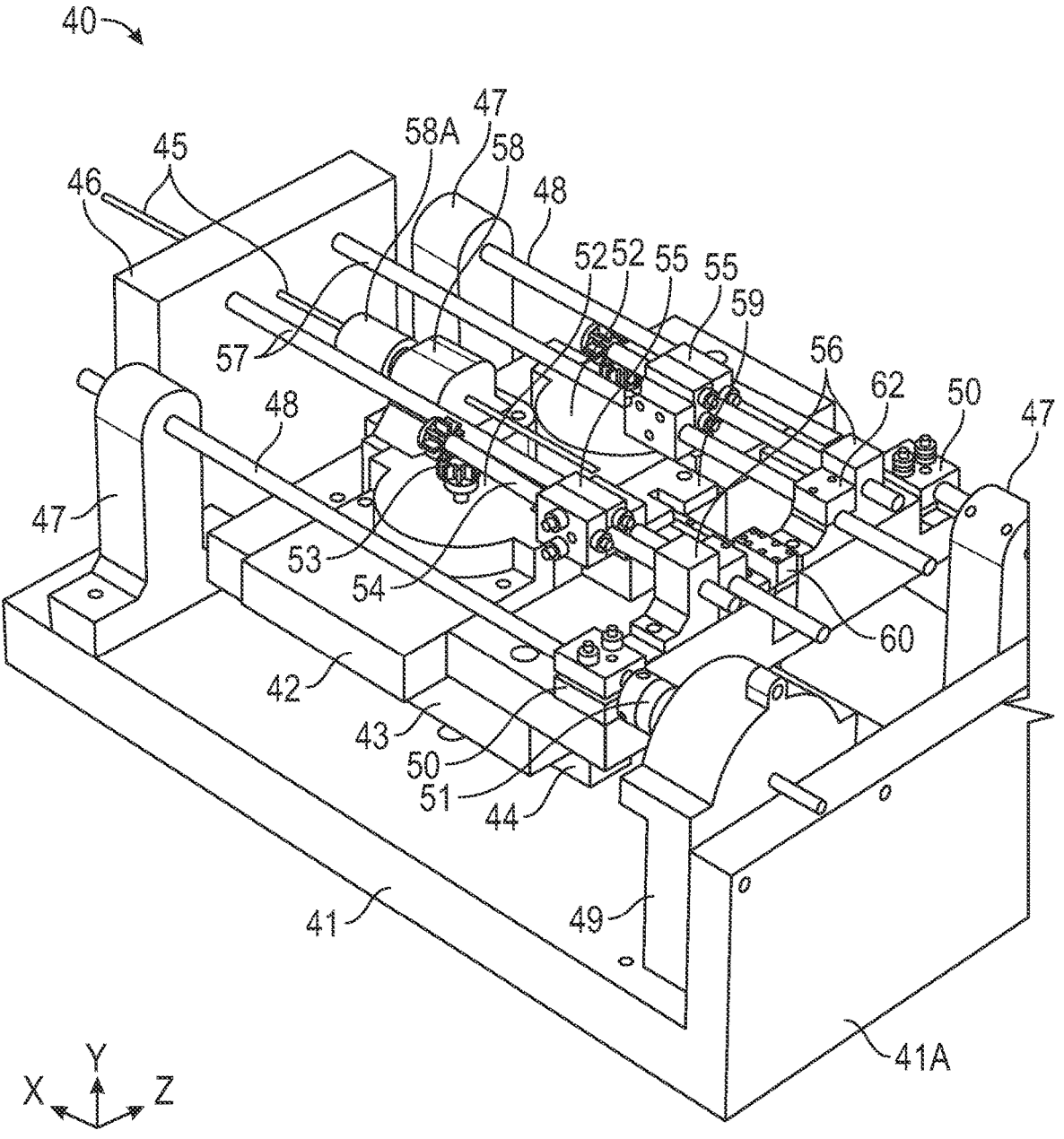
FIG. 2C is a perspective view of a first needle manipulation apparatus and an associated steerable surgical needle according to one embodiment of the present disclosure that may be used with a multi-axis positioning stage and may be operated within the bore of an MRI machine.

FIG. 2C is a perspective view of a first needle manipulation apparatus 40 and an associated steerable surgical tubular needle 45 according to an embodiment of the present disclosure, with the first needle manipulation apparatus 40 being configured to be supported by the upper mounts (39 in FIG. 2B) of a vertical positioning stage (30 in FIG. 2B). The first needle manipulation apparatus 40 includes a base plate 41, an end plate 41A extending upward from a rearward end of the base plate 41, and a plate-like needle guide 46 extending upward from a forward end of the base plate 41. A portion of the steerable surgical tubular needle 45 extends through the needle guide 46, and may rotate, but not translate, relative to the needle guide 46. A translating support plate 42 is arranged above the base plate 41 and includes carriage members 43 along an underside thereof that are movable in the x-direction along rails 44 affixed to the base plate 41. A piezoelectric rotary motor 49 and an associated threadless screw mechanism 51 (with screws 48 supported by screw guides 47) are arranged to cooperate with a coupling 50 joined to the translating support plate 42, to effectuate controllable movement of the translating support plate 42 in the x-direction. The threadless lead screw mechanism may utilize aluminum threadless lead screw nuts (McMaster-Carr, part nos. 2316N11 and 2316N12) to convert rotational movement into linear movement. The steerable surgical tubular needle 45 includes, within an internal longitudinal passage thereof, first and second tendons (e.g., 211, 212 in FIG. 5-6, or 231, 232 in FIG. 8), with the tendons being coupled to tendon holders 55 and being configured to be selectively tensioned using first and second piezoelectric rotary motors 52, thereby permitting the steerable surgical tubular needle 45 to be controllably bent in different directions. The piezoelectric rotary motors 52 have associated bevel gears 53 that cooperate with threadless screw mechanisms 54 (supported by tendon screw guides 56) to effectuate independent movement of the tendon holders 55 in the x-direction. Associated stabilizer rods 57 supported between the needle guide 46 and stabilizer rod supports 62 extend parallel to the threadless screw mechanisms 54, and are provided to stabilize and guide movement of the tendon holders 55. A collet nut 58A (having an internal collet, not shown) receives a portion of the steerable surgical tubular needle 45 between the needle guide 46 and a rotary piezoelectric motor 58 configured to effectuate rotation of the steerable surgical tubular needle 45. A further portion of the steerable surgical tubular needle 45 extends rearward to a stylet (i.e., movable tray) holder 59 having an associated linear piezoelectric motor 60 coupled with a guidewire (e.g., 233 in FIG. 10) extending within the needle 45 configured to effectuate movement of a stylet (e.g., 235 in FIG. 10) in a longitudinal direction through an internal passage of steerable surgical tubular needle 45, such as to permit collection of one or more tissue samples through the needle 45.

In use, the piezoelectric rotary motor 49 may be operated to move the translating support plate 42 in the x-direction, thereby advancing or returning the steerable surgical tubular needle 45 in the x-direction, to control x-translation when the steerable surgical tubular needle 45 is inserted into a body of a patient. The rotary piezoelectric motor 58 may be operated to control rotation of the steerable surgical tubular needle 45. The first and second piezoelectric rotary motors 52 may be operated to control movement of the tendon holders 55 in the x-direction, thereby selectively tensioning tendons within the steerable surgical tubular needle 45 and causing the steerable surgical tubular needle 45 to be bent in a desired direction. Each component of the needle manipulation apparatus 40 is devoid of ferrous materials.

Figure 2D:
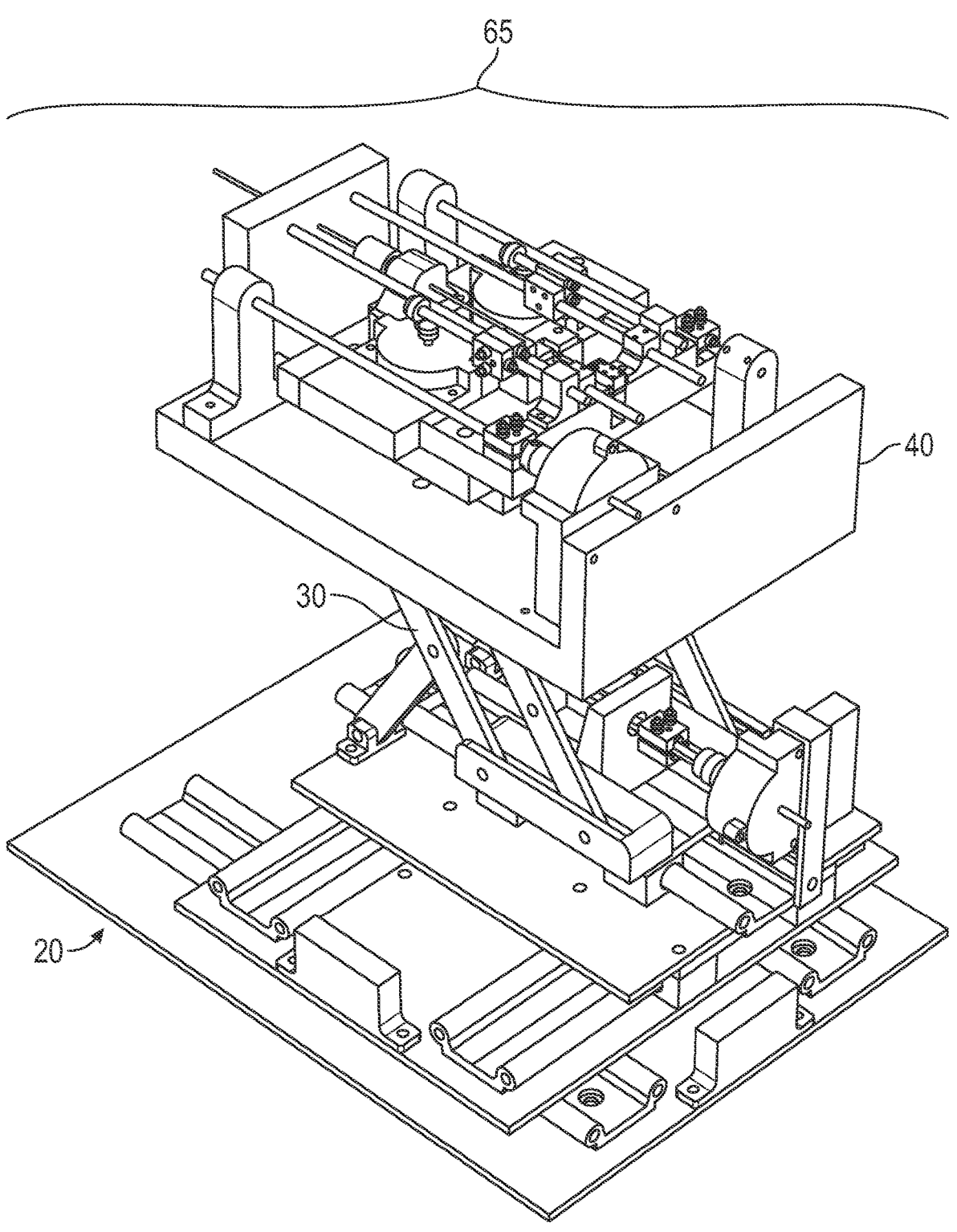
FIG. 2D is a perspective view of the first needle manipulation apparatus and steerable surgical needle of FIG. 2C being supported by the three-axis positioning stage shown in FIG. 2B.
Figure 2E:
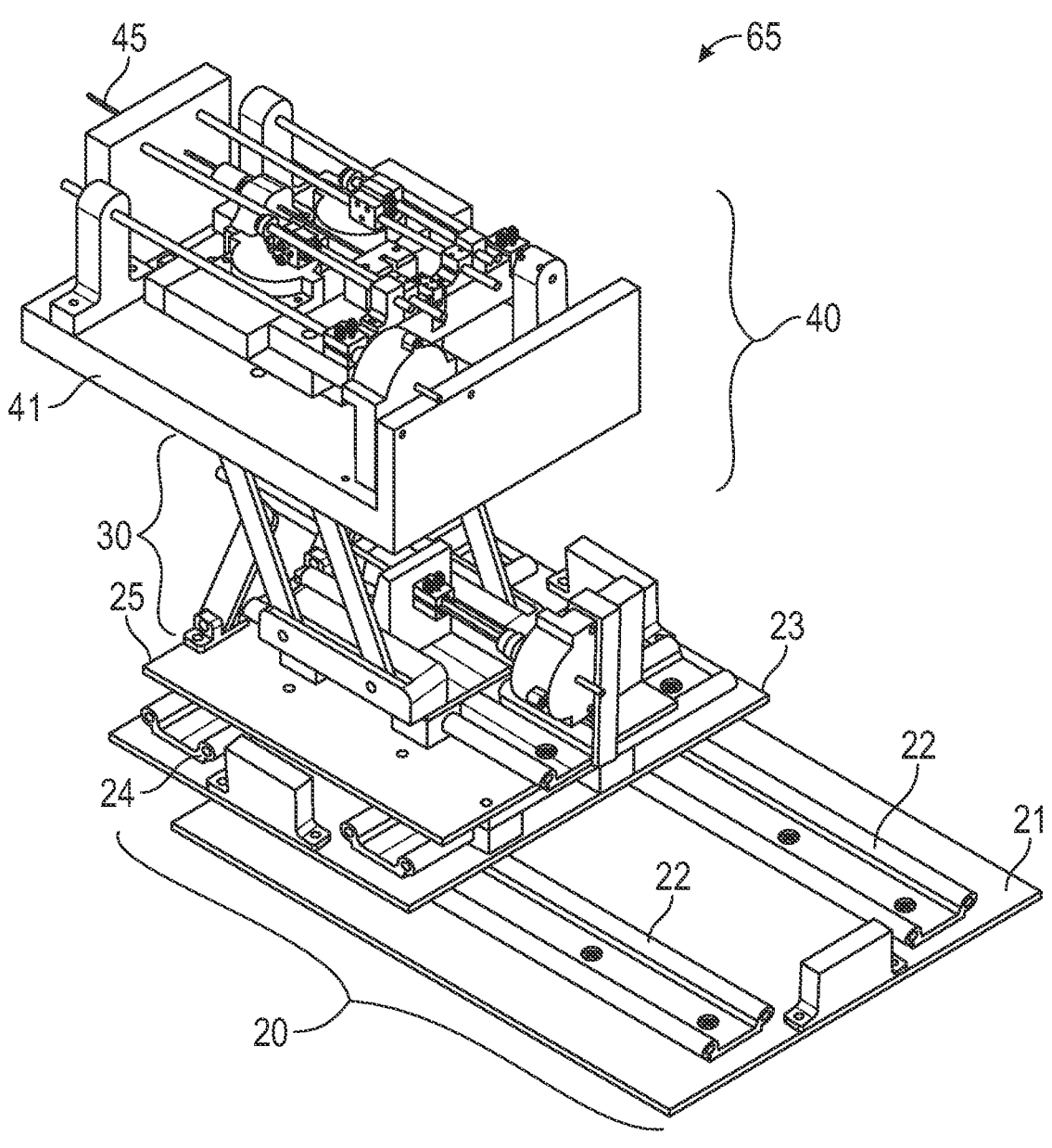
FIG. 2E is a perspective view of the items of FIG. 2D, with the vertical positioning stage and needle manipulation apparatus having been advanced in an x-direction by movement of a portion of the horizontal positioning stage.
Figure 2F:
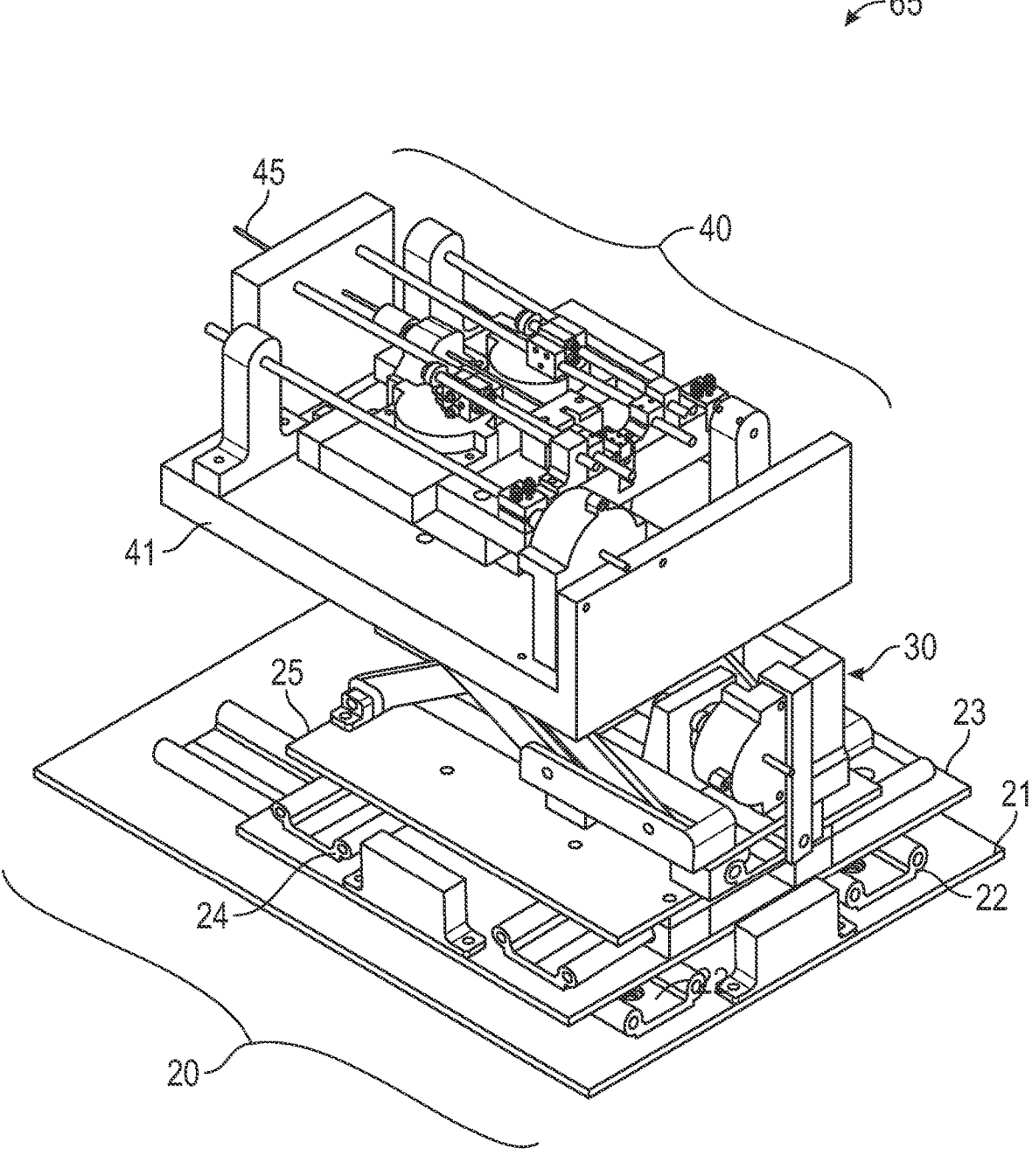
FIG. 2F is a perspective view of the items of FIGS. 2D and 2E, with the vertical positioning stage in a lower (retracted) position.

FIG. 2D is a perspective view of the first needle manipulation apparatus 40 and steerable surgical needle 45 of FIG. 2C being supported by the three-axis positioning stage (i.e., the vertical positioning stage 30 in combination with the horizontal positioning stage 20) of FIG. 2B, to form a multi-axially adjustable needle manipulation apparatus 65. As shown, the first needle manipulation apparatus 40 is substantially centered over the horizontal positioning stage 20, with the vertical positioning stage 30 being in an intermediate height position between a maximum height position and a minimum height position thereof. FIG. 2E shows the multi-axially adjustable needle manipulation apparatus 65 of FIG. 2D, following translation in the x-direction of the intermediate gantry plate 23 to a forward position, with the vertical positioning stage 30 remaining in the intermediate height position. FIG. 2F shows the multi-axially adjustable needle manipulation apparatus 65 of FIG. 2D, with the first needle manipulation apparatus 40 being substantially centered over the horizontal positioning stage 20, and with the vertical positioning stage 30 being in a minimum height position. All elements illustrated in FIGS. 2E and 2F have been previously described herein.

FIGS. 3A-3D illustrate a second needle manipulation apparatus 140 and an associated steerable surgical needle 145, being supported by a second vertical positioning stage 130 and configured to be operated within the bore of an MRI machine, according to one embodiment. Although a horizontal positioning stage is not shown in FIGS. 3A-3D, it is to be appreciated that in certain embodiments, the items of FIGS. 3A-3D may be mounted atop a horizontal positional stage 20 as shown in FIG. 2B.

Figure 3A:
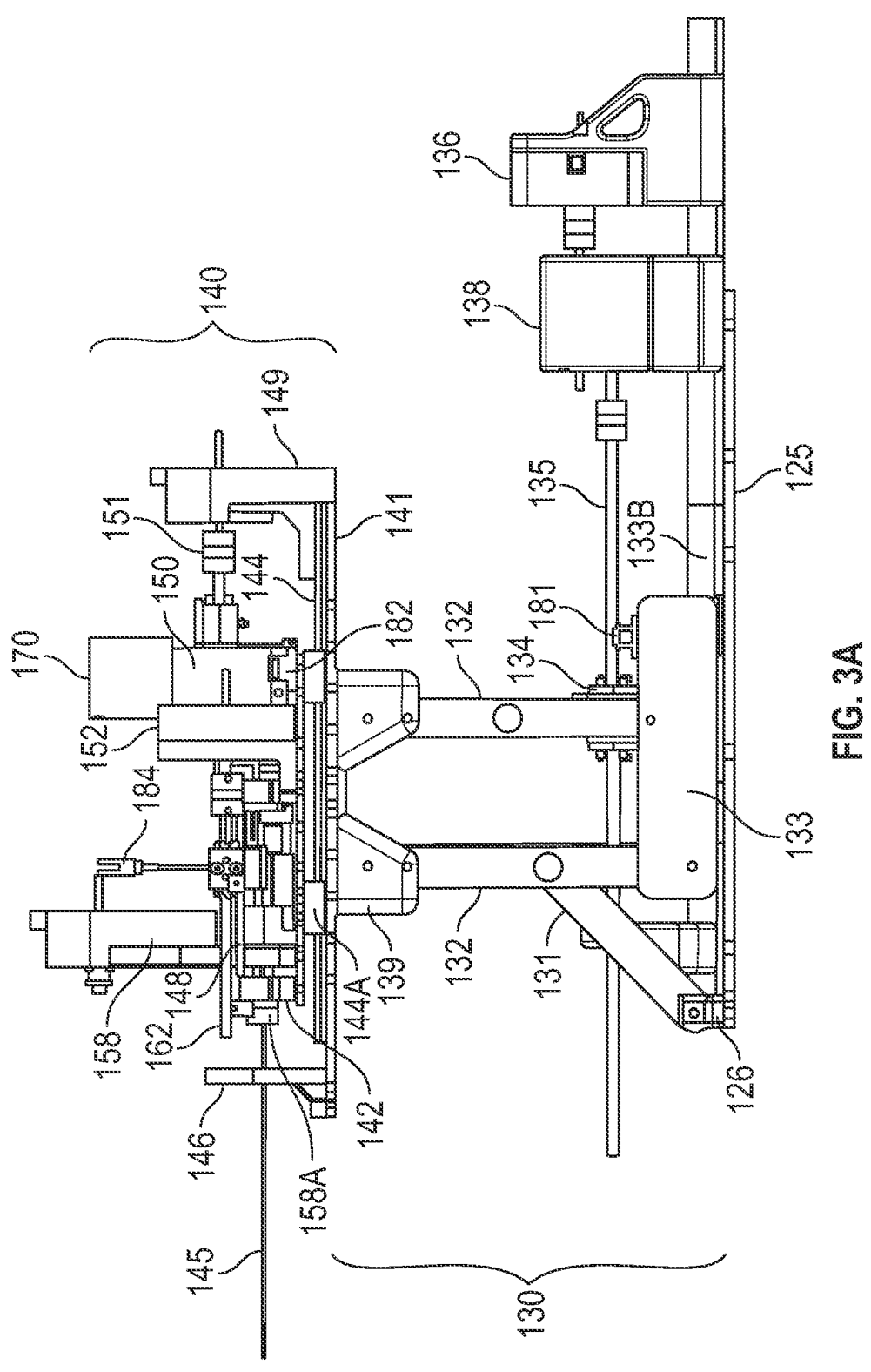
FIG. 3A is a side elevational view of a second needle manipulation apparatus and an associated steerable surgical needle, being supported by a vertical positioning stage that comprises a Scott-Russell mechanism and a rotary actuator, and configured to be operated within the bore of an MRI machine, according to one embodiment of the present disclosure.

As shown in FIG. 3A, the vertical positioning stage 130 comprises a Scott-Russell mechanism (including forward link 131, parallel links 132, traveling linkage 133, x-axis rail 33B, and pusher 134) as well as a piezoelectric rotary actuator 136 and a gear box 138 positioned atop an upper gantry plate 125 having associated pivot mounts 126. The piezoelectric rotary actuator 136 is coupled to the gear box 138, and a threadless lead screw mechanism 135 is arranged between the gear box 138 and the pusher 134. The pusher 134 is coupled to the traveling linkage 133, with associated carriage members (not shown) being configured to move along the x-axis rail 133B in order to permit movement of the traveling linkage 133 along the x-direction. Upper mounts 139 are pivotally mounted to upper ends of the parallel links 132 to enable mounting and provide support to base plate 141 of the needle manipulation apparatus 140. The forward link 131 is pivotally coupled between the pivot mounts 126 and leading ones of the parallel links 132. In use, rotation of the piezoelectric rotary actuator 136, coupled by the gear box 138 to the threadless lead screw mechanism 135, causes movement of the pusher 134 that is coupled to the traveling linkage 133. Movement of the traveling linkage 133, to which the parallel links 132 are pivotally coupled, causes pivotal movement of the parallel links 132, thereby causing the upper mounts 139 to rise or fall in the y-direction. Such movement permits vertical positional adjustment of the needle manipulation apparatus 140.

Figure 3B:
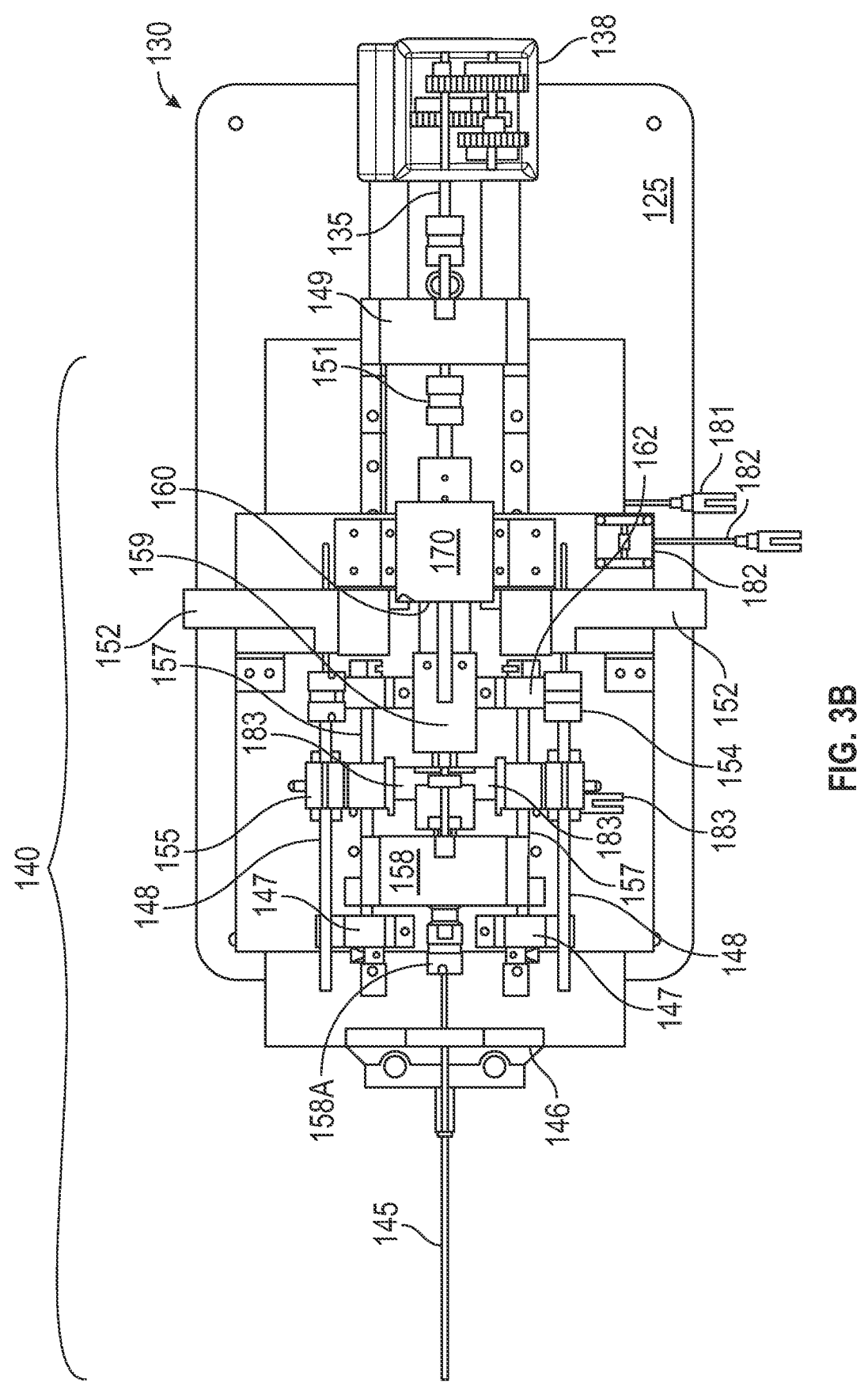
FIG. 3B is a top plan view of the items of FIG. 3A.
Figure 3C:
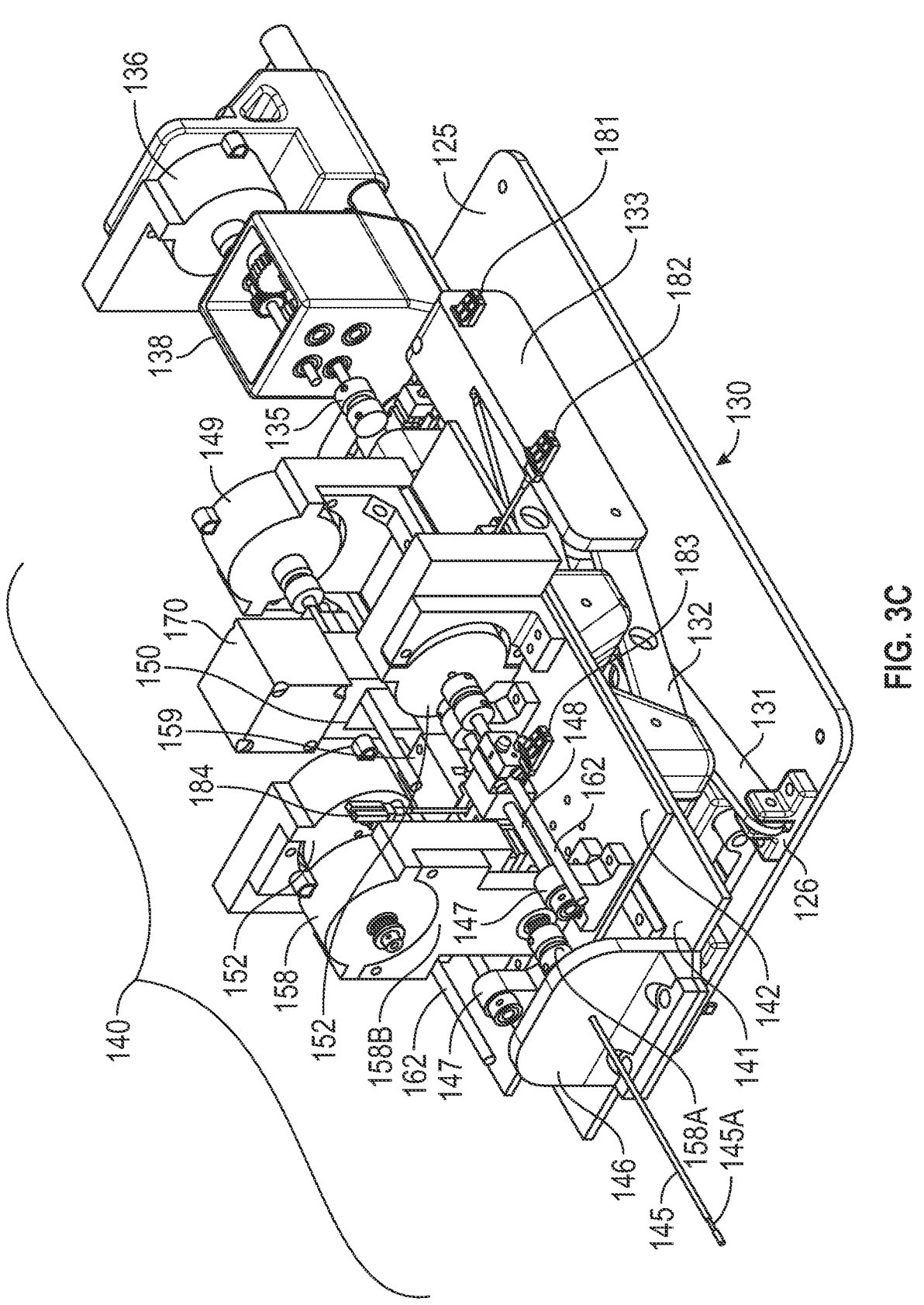
FIG. 3C is a perspective view of the items of FIGS. 3A and 3B, with the vertical positioning stage being in a lower (retracted) position.
Figure 3D:
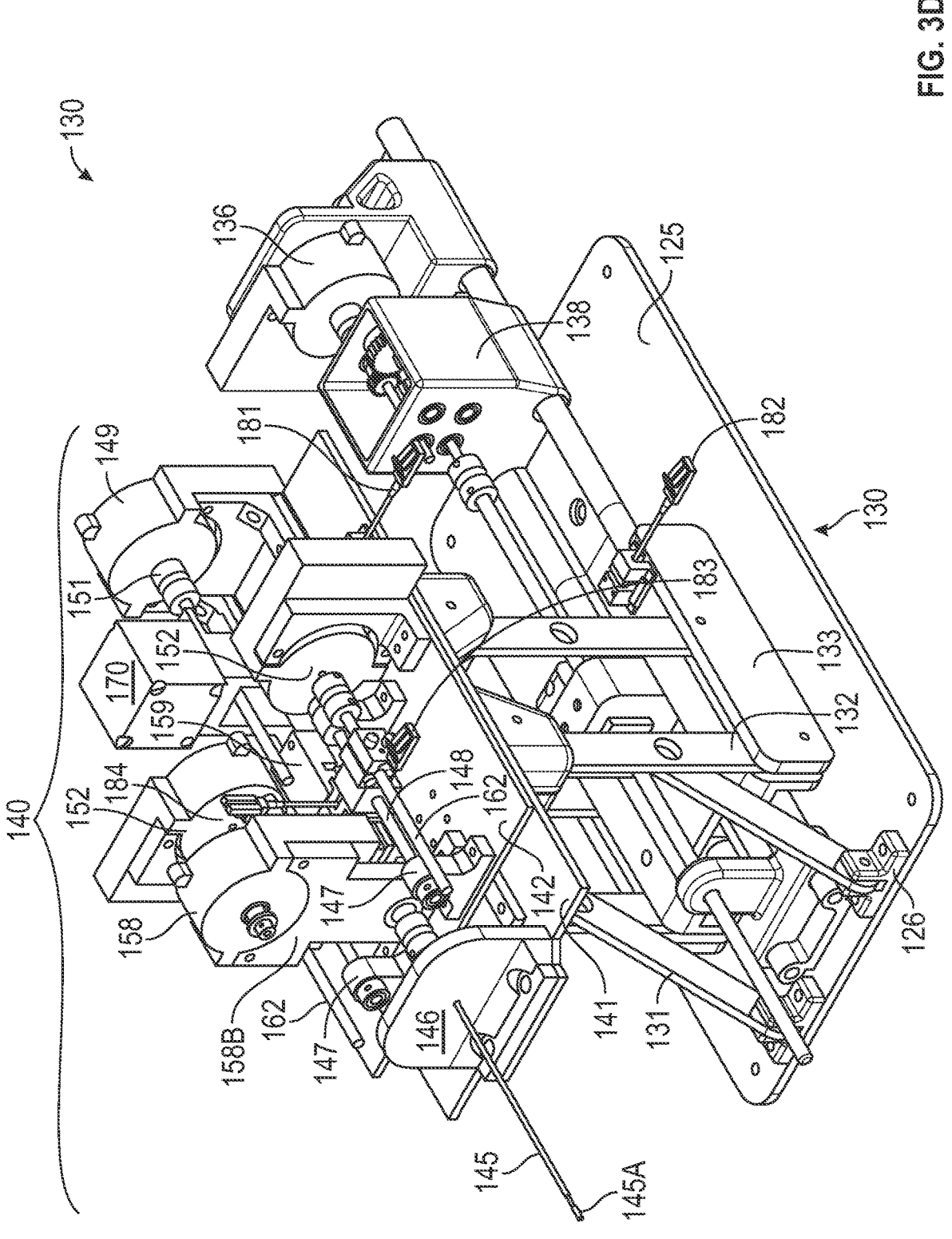
FIG. 3D is a perspective view of the items of FIGS. 3A-3C, with the vertical positioning stage being in an upper (extended) position.

Components of the needle manipulation apparatus 140 and associated steerable surgical tubular needle 145, together with the vertical positioning stage 130, are shown in FIGS. 3A-3D. FIG. 3A shows the vertical positioning stage 130 (and therefore also the needle manipulation apparatus 140 supported thereon) in a maximum height position. FIG. 3B is a top plan view of the items of FIG. 3A. FIG. 3C shows the vertical positioning stage 130 in a minimum height position, while FIG. 3D shows the vertical positioning stage 130 in an intermediate height position.

The needle manipulation apparatus 140 includes a base plate 141 with a plate-like needle guide 146 extending upward from a forward end of the base plate 141. A portion of the steerable surgical needle 145 extends through the needle guide 146, and may rotate, but not translate, relative to the needle guide 46. A translating support plate 142 is arranged above the base plate 141 and includes carriage members 144A along an underside thereof that are movable in the x-direction along rails 144 affixed to the base plate 141. A piezoelectric rotary motor 149 and an associated threadless screw mechanism 151 are arranged to cooperate with a coupling 150 joined to the translating support plate 142, to effectuate controllable movement of the translating support plate 142 in the x-direction. The steerable surgical tubular needle 145 includes, within an internal longitudinal passage thereof, first and second tendons (e.g., 211, 212 in FIG. 7-8, or 231, 232 in FIG. 10), with the tendons being coupled to tendon holders 155 and being configured to be selectively tensioned using first and second piezoelectric rotary motors 152, thereby permitting the steerable surgical tubular needle 145 to be controllably bent in different directions. The piezoelectric rotary motors 152 cooperate with threadless screw mechanisms 154 having screws 148 to effectuate independent movement of the tendon holders 155 in the x-direction. Associated stabilizer rods 157 supported between the needle guide 146 and stabilizer rod supports 162 extend parallel to the threadless screw mechanisms 154, and are provided to stabilize and guide movement of the tendon holders 155. A collet nut 158A (having an internal collet, not shown) receives a portion of the steerable surgical tubular needle 145 between the needle guide 146 and a rotary piezoelectric motor 158 (including transfer gearbox 158B, shown in FIG. 3C) that is configured to effectuate rotation of the steerable surgical tubular needle 145. A further portion of the steerable surgical tubular needle 145 extends rearward to a stylet (i.e., movable tray) holder 159 having an associated linear piezoelectric motor 160 (arranged below element 170 in FIG. 3B) coupled with a guidewire (e.g., 233 in FIG. 10) extending within the needle 145 configured to effectuate movement of a stylet (e.g., 235 in FIG. 10) in a longitudinal direction through an internal passage of steerable surgical tubular needle 145, thereby permitting collection of one or more tissue samples through the needle 145. Examples of piezoelectric rotary actuators that may be used include maximum torque 100-200 mNm, maximum speed 100 rpm models commercially available from Piezo Motion Corp, Sarasota, Florda FL, USA) and an example of a piezoelectric linear actuators that may be used includes model LT2020C-101E1A00, stall force 20N, 8 mm stroke, 101 mm drive rod, commercially available from PiezoMotor, Sweden.

With continued reference to FIGS. 3A-3D, the needle manipulation apparatus 140 further includes a fiducial frame 170 containing a plurality of fiducial markers, with individual fiducial markers (e.g., 174 in FIG. 3F) being supported by the fiducial frame 170 to be positioned in different respective planes. In certain embodiments, each fiducial marker contains MRI-visible high contrast fluid. The needle manipulation apparatus 140 additionally includes numerous encoders 181-184 (which may include linear or rotary encoders in certain embodiments) that are configured to provide positional information for various items. One encoder 181 is associated with the traveling linkage 133 and is used to provide information indicative of vertical position of the needle manipulation apparatus 140 that is supported by the vertical positioning stage 130. Another encoder 182 is associated with the translating support plate 142 initiated by the piezoelectric rotary motor 149 and is used to provide information indicative of x-direction horizontal position of the needle manipulation apparatus 140, which also corresponds to travel of the steerable surgical tubular needle 145 in the x-direction. Additional encoders 183 are associated with the tendon holders 155 and are used to provide information indicative of displacement of tendons used to effectuate bending of the steerable surgical tubular needle 145. A further encoder 184 is associated with an output of the piezoelectric rotary motor 158 (such as by sensing rotation of needle 145, or positions of gears within gearbox 158B) to provide information indicative of rotation (or rotational position) of the steerable surgical tubular needle 145. Another encoder (not shown) may be associated with the stylet holder 159, such as by sensing position of a stylet guidewire to provide information indicative of position of a stylet within a longitudinal passage of the steerable surgical tubular needle 145. Each component of the needle manipulation apparatus 140 and the vertical positioning stage 130 is devoid of ferrous materials.

In use, the piezoelectric rotary motor 149 may be operated to move the translating support plate 42 in the x-direction, thereby advancing or returning the steerable surgical tubular needle 45 in the x-direction, to control x-translation when the steerable surgical tubular needle 45 is inserted into a body of a patient. The rotary piezoelectric motor 158 may be operated to control rotation of the steerable surgical tubular needle 145. The first and second piezoelectric rotary motors 152 may be operated to control movement of the tendon holders 55 in the x-direction, thereby selectively tensioning tendons within the steerable surgical tubular needle 145 and causing the steerable surgical tubular needle 145 to be bent in a desired direction. The piezoelectric rotary motor 136 associated with the vertical positioning stage 130 may further be operated to effectuate movement of the needle manipulation apparatus 140 in a vertical direction. When the needle manipulation apparatus 140 is arranged within an MRI machine bore (e.g., 12 in FIG. 1), fiducial markers within the fiducial frame 170 may be imaged via the MRI machine (e.g., 10 in FIG. 1) and used by a control unit to identify position and orientation of the needle manipulation apparatus 140. Additionally, sensory information obtained from the encoders 182-185 (to detect movements initiated by the piezoelectric rotary motor 149, the piezoelectric rotary motor 158, and the piezoelectric motors 152) may be used by a control unit to identify translation, rotation, and bending, respectively, of the steerable surgical tubular needle 145, thereby determining position and orientation of the steerable surgical tubular needle 145 when inserted into a body of a patient within the MRI machine bore. If desired, the encoder 181 may additionally be used to detect vertical position of the needle manipulation apparatus 140. In certain embodiments, the control unit may be configured to apply kinematic functions in combination with the signals obtained from the plurality of encoders 182-185 to determine position and orientation of the steerable surgical tubular needle 145 within a patient. Thus, use of fiducial markers permits positional and orientational registration of the needle manipulation apparatus 140 relative to an MRI machine, and use of the encoders 182-185 permits positional and orientational registration of the steerable surgical tubular needle 145 to the needle manipulation apparatus 140; in combination, position and orientation of the steerable surgical tubular needle 145 can be determined relative to the MRI machine. In certain embodiments, additional fiducial markers may be applied on or in a body of a patient, so that position and orientation of the patient relative to the MRI machine, such that position and orientation of the steerable surgical tubular needle 145 can be determined relative to the body of the patient.

A steerable surgical apparatus incorporating the needle manipulation apparatus 140 may be used to realize precise needle displacement for needle axial insertion as well as needle bending for accurate targeting inside tissue of a patient in an MRI machine bore. The steerable surgical tubular needle 145 is intended to steer through the tissue based on the MRI imaging feedback and upon actuation commands received from a user (e.g., medical professional).

Figure 3E:
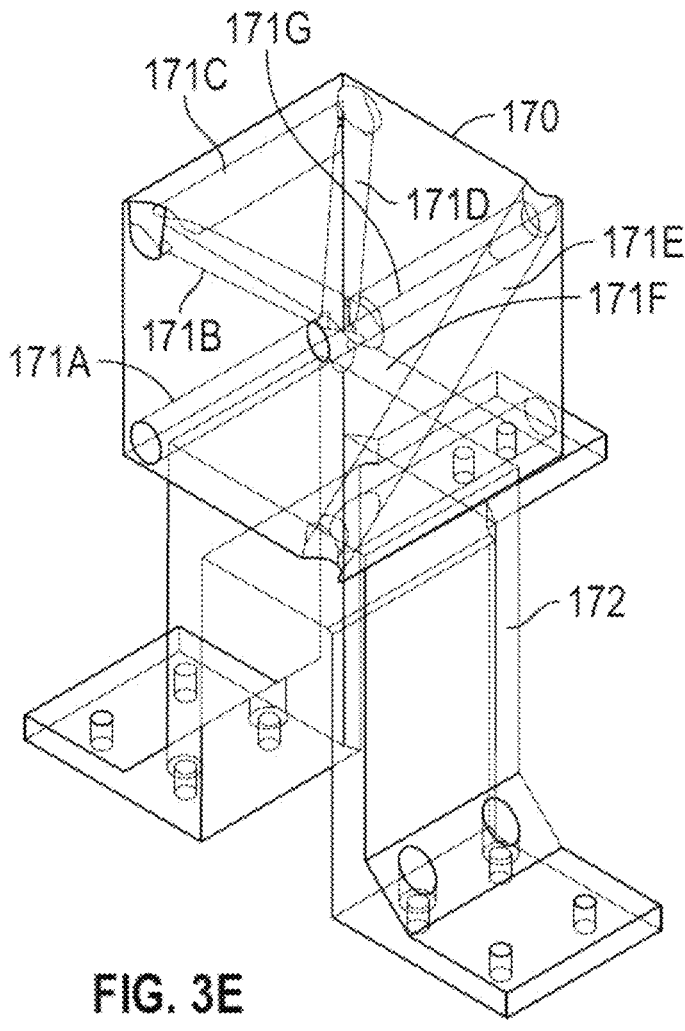
FIG. 3E is a perspective, partially transparent view of a fiducial frame of the second needle manipulation apparatus of FIGS. 3A-3D.
Figure 3F:
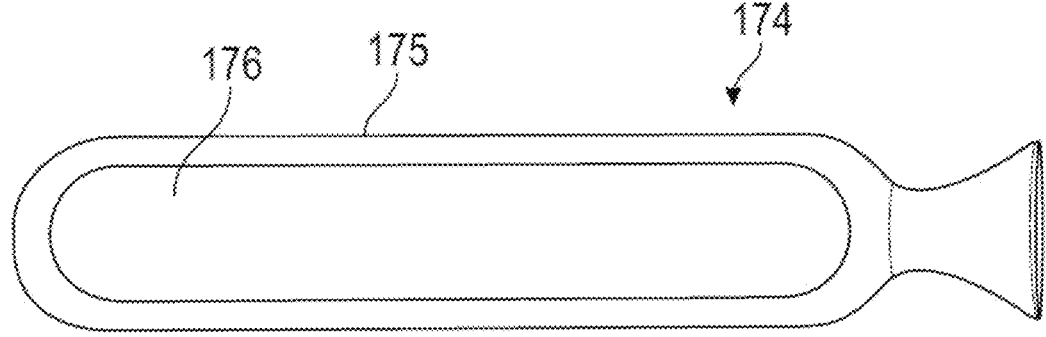
FIG. 3F is a side elevational view of a fiducial marker configured to be received by the fiducial frame of FIG. 3E, with the fiducial marker including a cavity containing MRI-visible high contrast fluid.

FIG. 3E is a perspective, partially transparent view of the fiducial frame 170 of the needle manipulation apparatus 140 of FIGS. 3A-3D. The fiducial frame 170 includes support legs 172 and defines seven channels 171A-171G respectively oriented in a Z-configuration in different planes, and each configured to receive a generally tubular fiducial marker (e.g., 174 in FIG. 3F). Presence of channels 171A-171G containing fiducial markers in multiple different planes aids in determination of position and orientation of the needle manipulation apparatus 140 of FIGS. 3A-3D when the fiducial markers are imaged by an MRI machine. In certain embodiments, fiducial markers may be highlighted in MR images to align a needle manipulation system with a patient's coordinate system, known as right-anterior-supine (RAS) coordinates. FIG. 3F is a schematic view of a fiducial marker 174 having a generally cylindrical body 175 with an internal cavity 176 containing MRI-visible high contrast fluid. One example of a suitable fiducial marker is MR-SPOT 121 commercially available from Beekley Systems, Bristol, Connecticut, USA.

Figure 4:
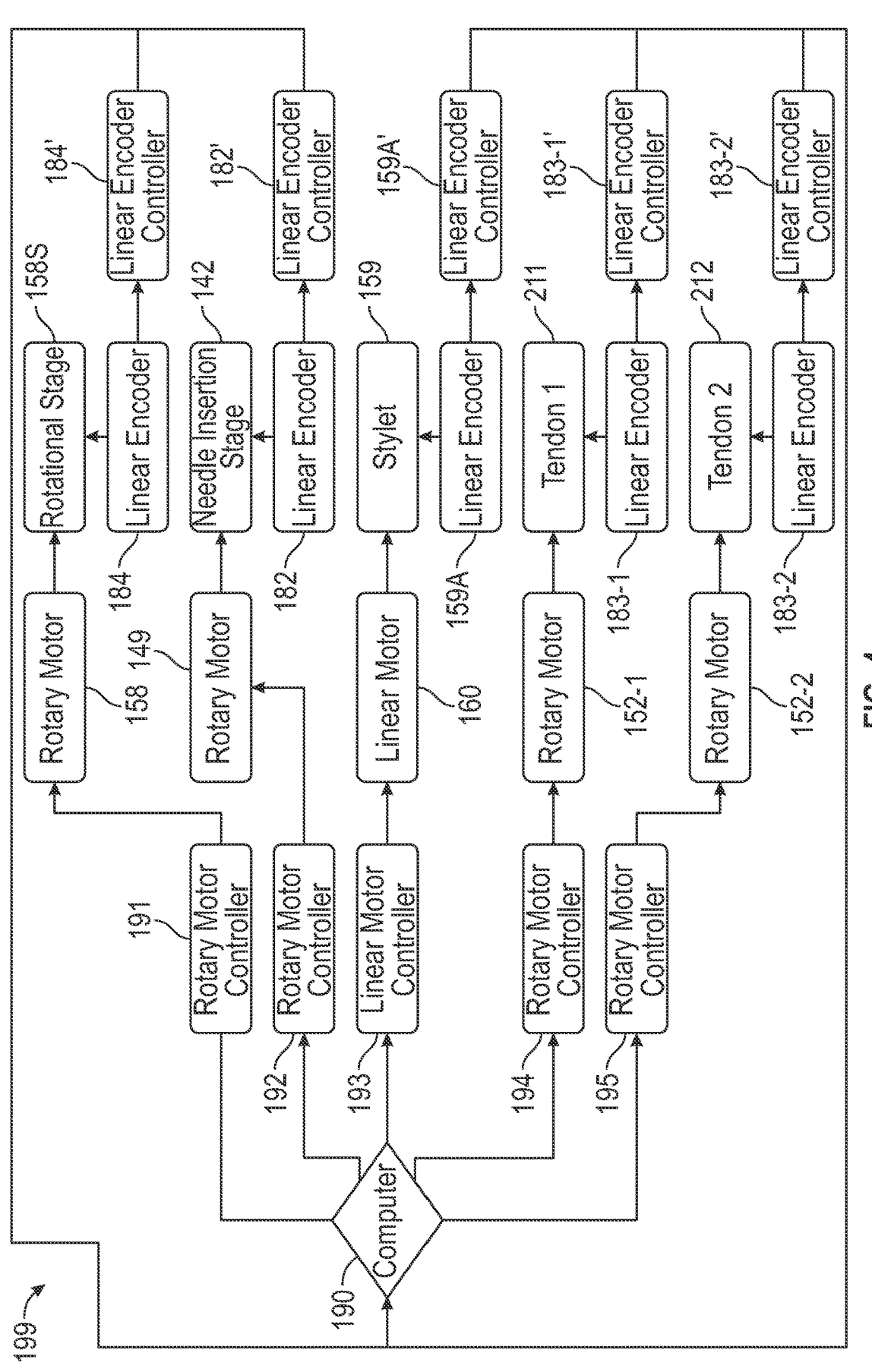
FIG. 4 is a schematic diagram showing interconnections between various actuating and sensory components of a steerable surgical apparatus including the needle manipulation apparatus shown in FIGS. 3A to 3D.

FIG. 4 is a schematic diagram showing interconnections between various actuating and sensory components of a steerable surgical apparatus including the needle manipulation apparatus 140 and steerable surgical tubular needle 145 shown in FIGS. 3A-3D. A control unit (e.g., computer) 190 is operatively coupled with multiple motor controllers 191-195, whether such controllers are rotary or linear in type. In certain embodiments, the control unit 190 may be arranged outside of an MRI bore and configured for wired or wireless (e.g., Bluetooth or the like) communication with the various controllers of FIG. 4. In certain embodiments, MRI-safe linear incremental position fiber optic sensors (MR343, Micronor Sensors, Ventura, CA, USA) with encoder film strips (EC-TD5334-1227, Micronor Sensors) plus corresponding MR340-1 controllers (Micronor Sensors) may be used A first rotary motor controller 191 is operatively coupled with a piezoelectric rotary motor 158 having an associated rotational stage 158S, wherein a linear encoder 184 having an associated linear encoder controller 184' is used to detect position of the rotational stage 158S (e.g., due to motion initiated by the piezoelectric rotary motor 158) corresponding to rotational position of the steerable surgical tubular needle 145. A second rotary motor controller 192 is operatively coupled with a piezoelectric rotary motor 149 having an associated needle insertion stage (e.g., translating support plate) 142, wherein a linear encoder 184 having an associated linear encoder controller 184' is used to detect position of the needle insertion stage 142 (e.g., due to motion initiated by the piezoelectric rotary motor 149), corresponding to translational (insertion length) position of the steerable surgical tubular needle 145. A third linear motor controller 193 is operatively coupled with a piezoelectric linear motor 160 associated with a guidewire of a stylet (i.e., moveable tray) internal to the steerable surgical tubular needle 145, wherein a linear encoder 159A having an associated linear encoder controller 159A' is used to detect position of the style guidewire (e.g., due to motion initiated by the piezoelectric linear motor 160), corresponding to longitudinal position of the stylet within the steerable surgical tubular needle 145. A fourth rotary motor controller 194 is operatively coupled with a piezoelectric rotary motor 152-1 arranged to apply tension to a first tendon 211, wherein a linear encoder 183-1 having an associated linear encoder controller 183-1' is used to detect position of the first tendon 211 (e.g., due to motion initiated by the piezoelectric rotary motor 152-1), wherein such position may be used to calculate tension applied by the first tendon 211 and thereby determine bending of the steerable surgical tubular needle 145 generated by the first tendon 211. A fifth rotary motor controller 195 is operatively coupled with a piezoelectric rotary motor 152-2 arranged to apply tension to a second tendon 212, wherein a linear encoder 183-2 having an associated linear encoder controller 183-2' is used to detect position of the second tendon 212 (e.g., due to motion initiated by the piezoelectric rotary motor 152-2), wherein such position may be used to calculate tension applied by the second tendon 211 and thereby determine bending of the steerable surgical tubular needle 145 generated by the second tendon 212.

A prototype steerable surgical apparatus according to the design of FIGS. 3A-3D was constructed, and subsystems thereof attained the following physical displacements: 132 mm for the Scott-Russell vertical positional stage; 102 mm for the needle insertion stage (horizontal); 10 mm for the stylet stage, and 90 mm for the horizontal positioning stage.

Figures 5, 6:
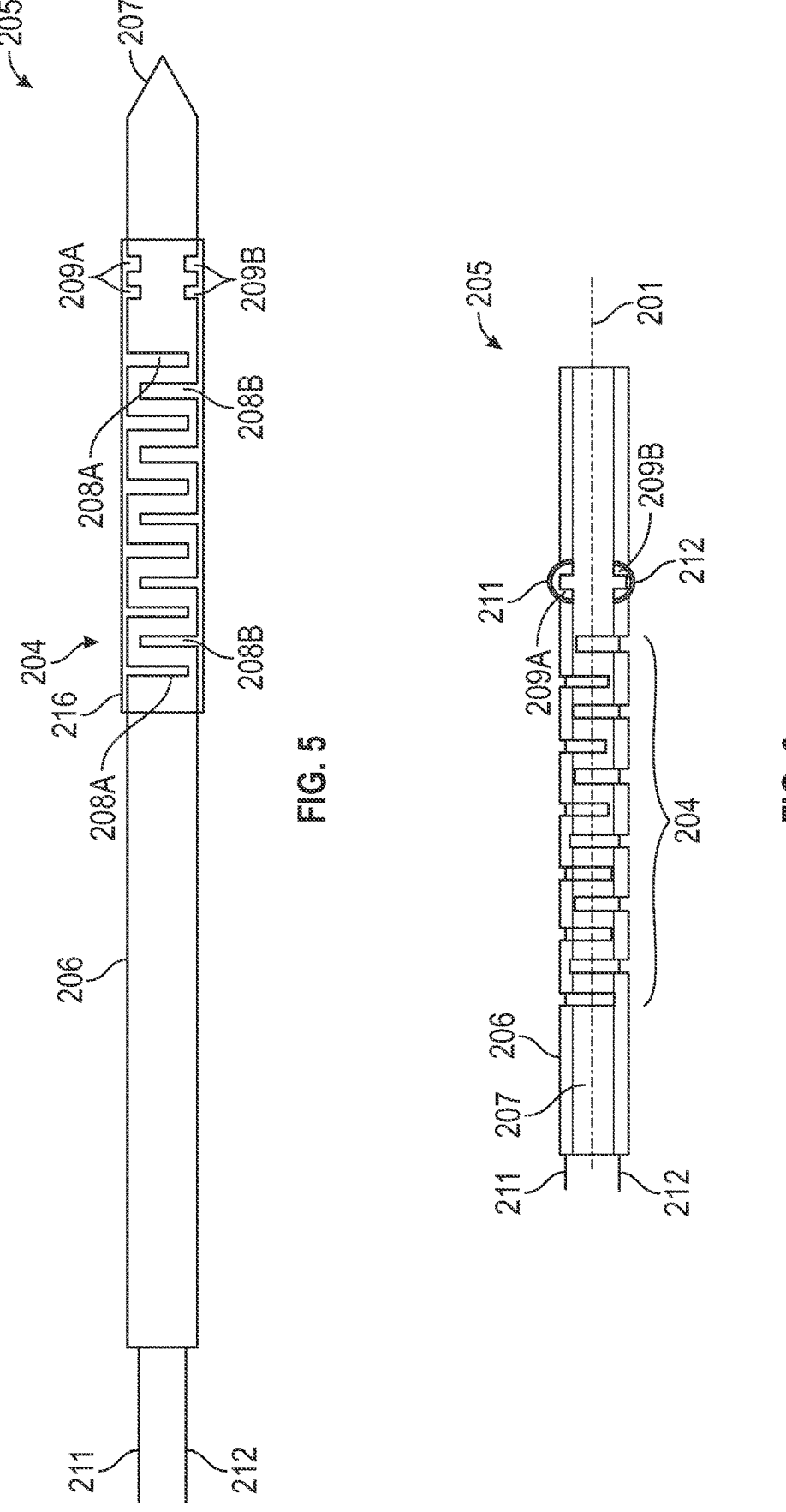
FIG. 5 is a top plan view of a portion of a steerable surgical tubular needle including multiple groups of transverse notches to provide a compliant flexure region and including first and second tendons extending to termination regions and being configured to be selectively tensioned to bend the needle at the compliant flexure region, with a covering material arranged over the compliant flexure region, according to one embodiment of the present disclosure.
FIG. 6 is a cross-sectional view of a portion of the steerable surgical tubular needle of FIG. 5.

FIG. 5 is a top plan view of a portion of a steerable surgical tubular needle 205 according to one embodiment. The steerable surgical tubular needle 205 includes a tubular body 206 and a pointed distal tip 207, and may be formed of a superelastic nitinol tube (e.g., 1.49 mm inner diameter (ID) and 2.00 mm outer diameter (OD), commercially available from Johnson Matthey, London, United Kingdom). Multiple groups of transverse notches 208A, 208B are defined in the tubular body (e.g., using an ultraviolet laser cutter machine (Confluent Medical, Scottsdale, Arizona, USA) to provide a compliant flexure region 204 (e.g., having a length of 13.3 mm). Although only two groups of transverse notches 208A, 208B are shown in an interleaved fashion, it is to be appreciated that in certain embodiments, one or more additional group(s) of notches may be provided, whether in fully interleaved, partially interleaved, or non-interleaved fashion. First and second tendons 211, 212 (e.g., 0.10 mm nitinol wires) extend through a longitudinal passage (207 in FIG. 6) of the tubular body, and may be looped in and out of holes 209A, 209B (e.g., 0.25 mm in diameter) defined in the tubular body 206 (to form loops 211', 212' in FIG. 6 proximate to the distal tip 207) and fixed to drive needle bending when pulled. The tendons 211, 212 are configured to be selectively tensioned to drive bending of the needle 205 at the compliant flexure region 204. The compliant flexure section 204 may be covered by heat shrink tubing 216 (e.g., polyethylene terephthalate (PET) material having 13 μm thickness). PET material is biocompatible and sterilizable with ethylene oxide. FIG. 6 is a cross-sectional view of a portion of the steerable surgical tubular needle 205 of FIG. 5 without the heat shrink tubing, showing the tendons 211, 212 within the longitudinal passage 207, and schematically illustrating a neutral axis 201 about which the flexure region 204 may be bent by selectively tensioning the tendons 211, 212.

Figure 7A:
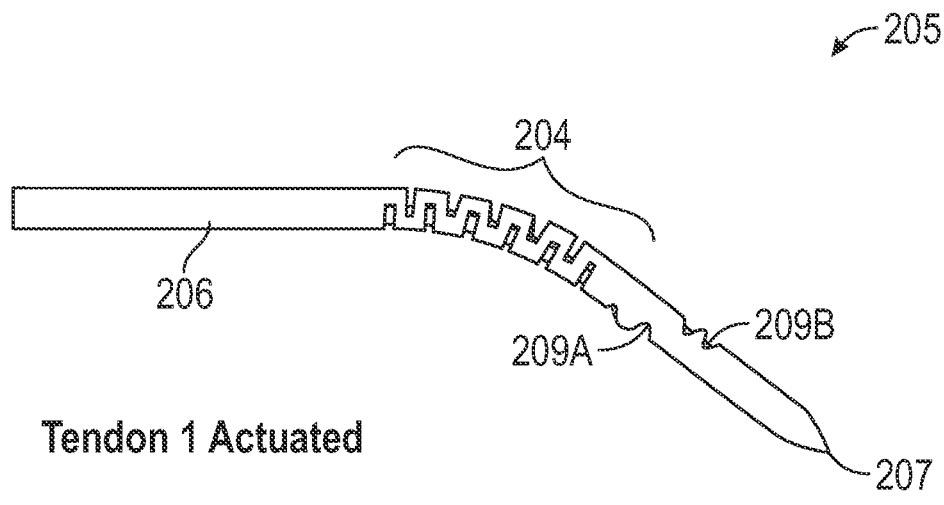
FIGS. 7A and 7B are top plan views showing the steerable surgical tubular needle being bent in first and second directions due to selective tensioning of the first and second tendons.
Figure 7B:
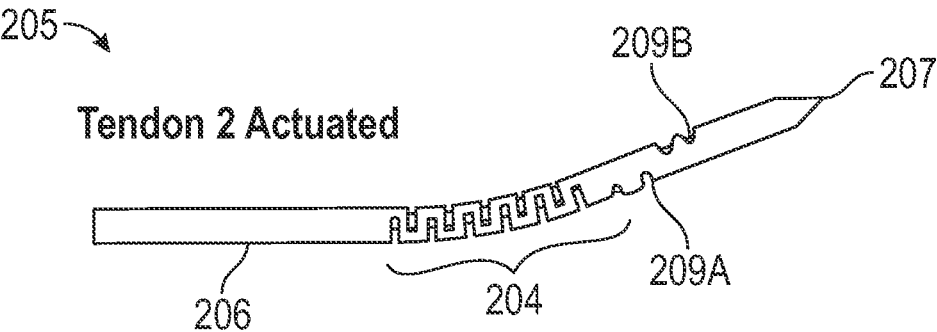

FIGS. 7A and 7B are top plan views of portions of the steerable surgical tubular needle 205 being bent in first and second directions, respectively, due to selective tensioning of the first and second tendons (211, 212 in FIGS. 5-6). FIG. 7A shows the steerable surgical tubular needle 205 being bent along the flexure region 204 in a first direction due to activation of a first tendon, and FIG. 7B shows the steerable surgical tubular needle 205 being bent along the flexure region 204 in a second direction due to activation of a second tendon.

Figure 8:
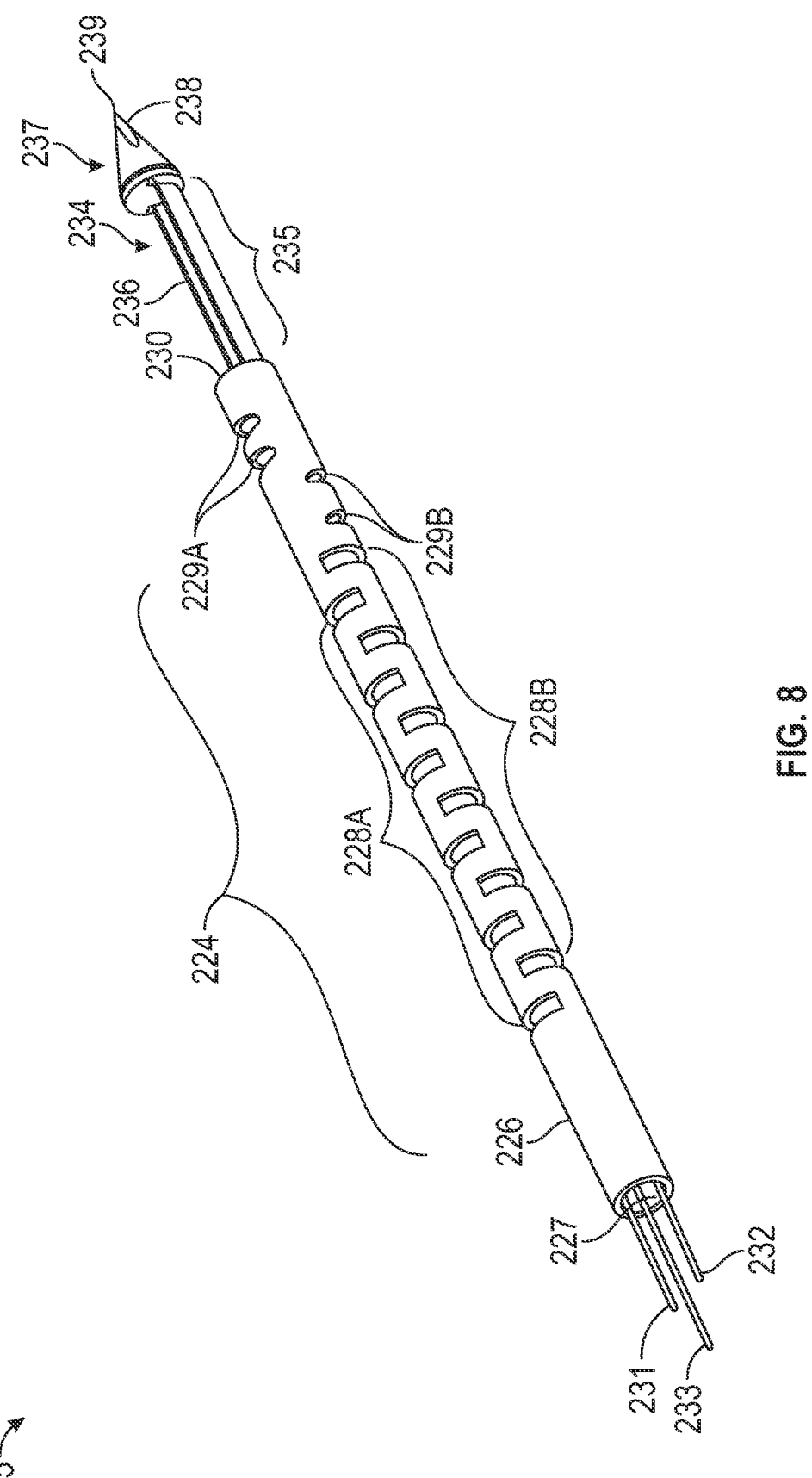
FIG. 8 is a perspective view of a steerable surgical tubular needle according to one embodiment of the present disclosure, including features similar to the tubular needle of FIG. 5, with addition of a moveable tray member (also referred to herein as a stylet) coupled with a guidewire internal to the tubular needle and configured to move longitudinally through a passage of the tubular needle for collection of a tissue sample.

FIG. 8 is a perspective view of a steerable surgical tubular needle 225 according to one embodiment, including a tubular body 226 into which differently oriented groups of transverse slits 228A, 228B are defined to form a compliant flexure region 224. Holes 229A, 229B are provided between the flexure region 224 and a distal end 230 of the tubular body 226, for receiving tendon members 231, 232 that may be selectively tensioned to deflect (bend) the steerable surgical tubular needle 225 at the flexure region 224 to change the shape thereof. A moveable tray member (also referred to as a stylet) 235 with a corresponding pointed tip member 237 are arranged at a distal end 230 of the body structure 226, with the moveable tray member 235 being shown in an extended or deployed state. The moveable tray member 235 includes a tray 236 having a curved profile, with a lateral opening 234 positioned adjacent to the tray 236. The tip member 237 is generally conical in shape and includes blade surfaces 238 and a pointed tip 239. In use, the moveable tray member 235 may be extended or retracted using a guidewire 233 extending through a longitudinal passage 227 internal to the body structure 226. When the steerable surgical device 225 is inserted to a desired position, the moveable tray member 235 may be deployed, and tissue may be admitted into the lateral opening 234. The distal end 230 of the tubular body 226 may include a cutting surface, such that when the moveable tray member 235 is retracted, a sample of tissue received into the lateral opening 234 into the tray 236 may be cut from the bulk tissue, and received within the longitudinal passage 227 of the steerable surgical tubular needle 225. In certain embodiments, the tip member 237 is not retractable through the longitudinal passage 227 with the moveable tray member 235.

Having described the foregoing components, robot registration and kinematics will now be described. As noted previously, the fiducial frame 170 with multiple fiducial markers 174 may be highlighted in MR images to align a needle manipulation apparatus with a patient's coordinate system, known as right-anterior-supine (RAS coordinates). Using multiple (e.g., seven) fiducial markers across various slices, a six degrees of freedom (6-DOF) position and orientation of a robotic needle manipulation apparatus relative to the scanner origin are computed. Following the registration process, a control unit for a needle manipulation apparatus can accept target coordinates in RAS image coordinates. The following sequence of homogeneous transformations is then employed to find the tip location of a steerable surgical tubular needle in MR RAS image coordinates. A first transformation is provided in the following Equation 1:

$$T_{Tip}^{RAS} = T_Z^{RAS} \cdot T_{Rob}^Z \cdot T_{Tip}^{Rob} \qquad \text{[Equation 1]}$$

where $$T_{Tip}^{RAS}$$

represents the position of the needle tip within the RAS patient coordinate system, $$T_Z^{RAS}$$

denotes the fiducial's coordinates in RAS coordinates obtained through the Z-frame fiducial-based registration process, $$T_{Rob}^Z$$

indicates the location of the needle guide 146 of FIGS. 3A-3D relative to the translating support plate 142 of FIGS. 3A-3D (which aligns with the fiducial's 6-DOF coordinate) determined through the forward kinematics of the robot as described below, and $$T_{Tip}^{Rob}$$

is the position of the needle tip relative to the front face of the needle guide on the robot (typically the point of entry into the skin) as defined by the kinematics presented herein.

During operation, a target position $$T_{Tip}^{RAS}$$

is chosen within the MR image volume. This target position $$T_{Tip}^{RAS}$$

is then transmitted from the planning workstation to the robot, which employs inverse kinematics to determine the necessary positions of the actuators. The estimated positions are subsequently relayed to the robot controller to actuate the piezoelectric actuators. Using the navigation coordinate relationship, the kinematics can be integrated into a kinematic chain to determine the position and orientation of the needle tip. The robot's vertical movement is facilitated by the actuated Scott-Russell mechanism, where linear motion in the superior-inferior direction translates into motion along the anterior-posterior (AP) axis. The forward kinematics of the robot relative to the fiducial frame are specified by the following Equations 2:

$$y = \sqrt{L^2 - \left(L - \frac{q_1 \cdot p}{360}\right)^2} + y_{offset} \qquad \text{[Equations 2]}$$

$$z = \frac{q_2 \cdot p}{360} + q_3 + z_{offset}$$

where $q_1$, $q_2$, $q_3$ are actuator's space motion of the y- and z-axis rotary motor ration in degrees, and needle driver insertion translation in mm, respectively, and L is the length of the bars in the Scott-Russell mechanism. The offset terms in Equations 2 are corresponding to the homogeneous transformation matrix $$T_{Rob}^Z$$

in Equation 1 hereinabove. Linear motions of the lead screws (with p as the lead screw pitch) are realized by the rotary piezoelectric actuator motions.

Figure 9:
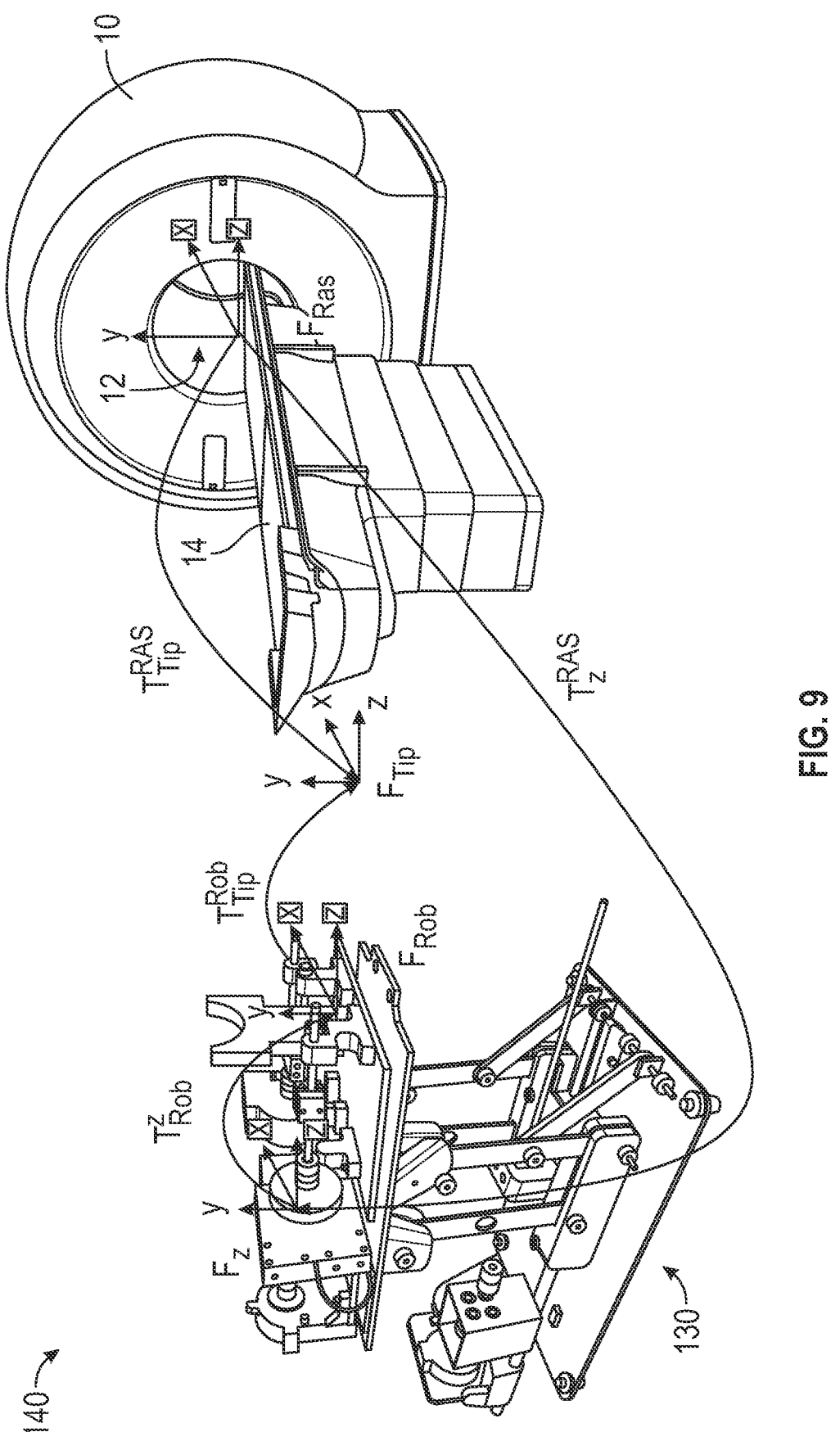
FIG. 9 provides perspective views of the MRI machine of FIG. 1 as well as the needle manipulation stage and vertical positioning stage of FIGS. 3A-3D, with schematic illustration of coordinate transformation to promote positional and orientation registration between the needle manipulation stage and the MRI machine.

FIG. 9 schematically illustrates the foregoing transformations. Such figure provides perspective views of the MRI machine 10 and MRI machine bore 12 of FIG. 1 as well as the needle manipulation apparatus 140 and vertical positioning stage 130 of FIGS. 3A-3D, with schematic illustration of coordinate transformation to promote positional and orientation registration between the needle manipulation apparatus 140 and the MRI machine 10.

Kinematics of the flexure section of a steerable surgical needle with N notches (e.g., notches as shown in FIGS. 5-8) will now be described.

For a steerable needle with N notches, the bending angle of the compliant flexure section ($\theta_{total}$) is calculated by the following Equation 3:

$$\theta_{total} = \frac{N-1}{2}\theta_{notch} \qquad \text{[Equation 3]}$$

where $\theta_{notch}$ is the bending angle of a single notch, calculated using Castigliano's second theorem as Equation 4:

$$\theta_{notch} = \frac{\partial U}{\partial M_r} \qquad \text{[Equation 4]}$$

where U is the total internal energy and $M_r$ is the moment at the cross section, given by the following Equations 5 and 6:

$$U = \frac{1}{2}\int_{-(d-r_o)}^{d-r_o}\int_{-\frac{t}{2}}^{\frac{t}{2}}\frac{M_r(x)^2 z^2 w(x)}{EI^2(x)}dzdx \qquad \text{[Equation 5]}$$

$$M_r(x) = M - F_1 \times (d - r_o - x) \qquad \text{[Equation 6]}$$

where d is the depth of the notch, t is the distance between two notches, $r_o$ and $r_i$ are the outer and inner radii of the nitinol tube, respectively, E is the young modulus, and $F_1$ is the force applied on each notch. It should be noted that the effects of gravity are not considered in this disclosure. w(x), I(x), and M are width of the section, second moment of area with respect to the y-axis, and the moment applied to the section, found by the following Equations 7, 8, and 9:

$$w(x) = \sqrt{r_0^2 - x^2} - \sqrt{r_i^2 - x^2} \qquad \text{[Equation 7]}$$

$$I(x) = \frac{1}{12}t^3 w(x) \qquad \text{[Equation 8]}$$

$$M = F_1 \times \left(d - (r_o - r_i) - \frac{t_d}{2}\right) \qquad \text{[Equation 9]}$$

where $t_d$ is the tendon diameter.

For the dimensions listed in the following Table 1 (in which $F_1$ is used to calculate the average bending for a single notch), about 10 degrees of bending angle has been estimated for each notch, and an overall bending angle of 55 degrees has been estimated for the steerable surgical needle (See Equation 3).

TABLE 1

| Dimensions of notches for steerable surgical needle (units in mm) | | | | | |
|---|---|---|---|---|---|
| Length (l) | Internal radius ($r_i$) | External radius ($r_o$) | $\bar{y}$ | Depth (d) | Inter-notch distance (t) |
| 13.280 | 0.745 | 1.00 | 1.450 | 1.680 | 0.460 |

To properly control the actuators to pull the internal tendons and consequently realize a desired bending angle at active needle tip, kinematic analysis of the compliant flexure section is needed. The kinematic analysis provides a relationship between the tendon displacement and the bending angle. For the bidirectional active needle, presented in this work, the kinematic analysis utilizes the following Equations 10 to 15:

$$\Delta L = f(\theta, N, d) + \epsilon(\theta, d, t, N) \qquad \text{[Equation 10]}$$

where $\Delta L$ is the tendon displacement, e is the bending angle, N is the number of notches, d is the notch depth, and t is the gap between two consecutive notches. The first and second terms refer to the kinematic and the tendon elongation, respectively. The kinematic term is:

$$f(\theta, N, d) = N \cdot r_t \cdot \sin(\delta\theta) \qquad \text{[Equation 11]}$$

where $\delta\theta$ is the bending angle of each notch, which is part of the total bending angle ($\theta = N.\delta\theta$), and $r_t$ can be found by:

$$r_t = d - \frac{(OD - ID)}{2} - \frac{t_d}{2} \qquad \text{[Equation 12]}$$

where OD is the outer diameter of the tube, ID is the inner diameter of the tube, and $t_d$ is the diameter of the tendon. The tendon elongation term is approximated by:

$$\epsilon(\theta, d, t, N) = E_{tendon} \cdot F_{tendon}(\theta, d, t, N) \qquad \text{[Equation 13]}$$

where $F_{tendon}$ is the tendon tension measured experimentally, and $E_{tendon}$ is the tendon compliance approximated by the relationship between the tendon length ($L_{tendon}$), and the Young's modulus of the nitinol tendon ($E_{tendon}$) as:

$$E_{tendon} = \frac{L_{tendon}}{A \cdot E_{tendon}} \qquad \text{[Equation 14]}$$

For the steerable surgical tubular needle disclosed herein, the parameters listed in Table 1 are fed into the equations. The relationship between the force and the bending angle, $F_{tendon}$ ($\theta$, d, t, N), is obtained experimentally as:

$$F_{tendon}(\theta, d, t, N) = 0.2743\theta \qquad \text{[Equation 15]}$$

Figure 10:
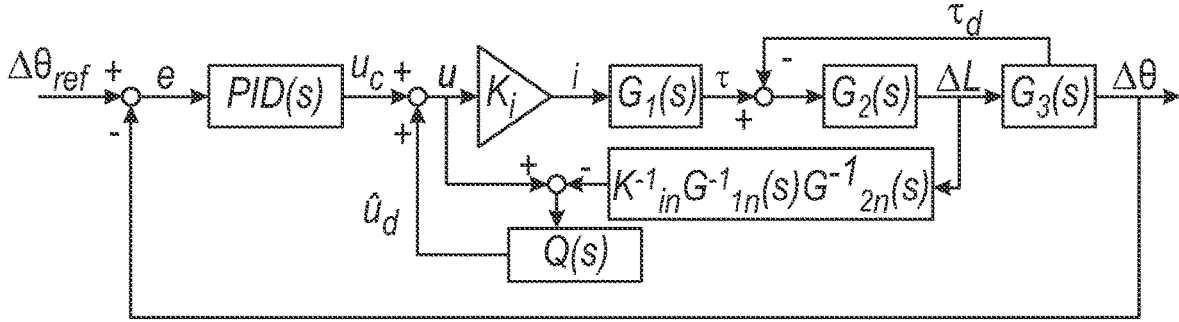
FIG. 10 is a control system diagram for a closed-loop PID controller (control scheme) configured to realize a desired angle at a tip of a steerable surgical tubular needle useable with embodiments of the present disclosure.

FIG. 10 is a control system diagram for a closed-loop PID controller that was designed and implemented to realize a desired bending angle at the tip of the steerable surgical tubular needle. In FIG. 10, $\Delta\theta$ is the bending angle output of the active needle that is provided as a feedback in the closed-loop system, $\Delta\theta_{ref}$ is the reference (desired) bending angle with respect to the measured angle ($\Delta\theta$), e is the error of the system (e=$\Delta\theta_{ref}$–$\Delta\theta$), and $\Delta L$ is the tendon displacement. The transfer functions, shown in the system diagram, are $K_i$, $G_1(s)$, $G_2(s)$, and $G_3(s)$, that describe relationships between control input (u) vs. current (i), current (i) vs. actuator torque (T), actuator torque (T) vs. actuator stroke ($\Delta L$), and actuator stroke ($\Delta L$) vs. $\Delta\theta$, respectively. Since the electrical response of the actuator based on the current input is faster compared to other mechanical responses in the diagram, $G_1(s)$ is assumed as a constant value. $G_2(s)$ is designed as a second-order system. The linear stroke of the actuator ($\Delta L$) is measured experimentally to build dynamics with respect to the actuator torque. The control error, e, is used as the input of the PID controller, producing the PID control input (u). $G_3(s)$ represents the kinematic model of the active needle (described above). The relationship (and the transfer function) between $\Delta L$ and u could be found with the following Equation 16:

$$\Delta L = (K_i)\ G_1(s)\ G_2(s)(u) \qquad \text{[Equation 16]}$$

The system is subject to a disturbance torque ($T_d$) imposed by the stiffness of the flexure section of the active needle on the motor, and thereby cannot have a consistent response. To avoid undesired responses (e.g., overshoot or non-consistent steady state error) and to develop a precise and robust position controller, a disturbance observer was added to the PID controller. The disturbance observer loop estimates Ta in form of a control input ($\hat{u}_d$) using the following Equation 17:

$$\hat{u}_d = \left(u - \Delta L \cdot K_{in}^{-1} \cdot G_{1n}^{-1} \cdot G_{2n}^{-1}\right)Q \qquad \text{[Equation 17]}$$

where $$K_{in}^{-1},\ G_{1n}^{-1},$$

and $$G_{2n}^{-1}$$

are nominal forms of the functions, $K_i$, $G_1$, and $G_2$, respectively, which are estimated with the system identification toolbox (MATLAB R2022b, The Mathworks Inc.) from the measured response of these functions with respect to a chirp signal input, and Q is a second-order low-pass filter as $$Q(s) = w_c^2 / (s^2 + 2w_c s + w_c^2),$$

where $w_c$ is cut-off frequency. Then, $\hat{u}_d$ is added to $u_c$ resulting in the control input, u according to the following Equation 18:

$$u = u_c + u_d \qquad \text{[Equation 18]}$$

Figure 11A:
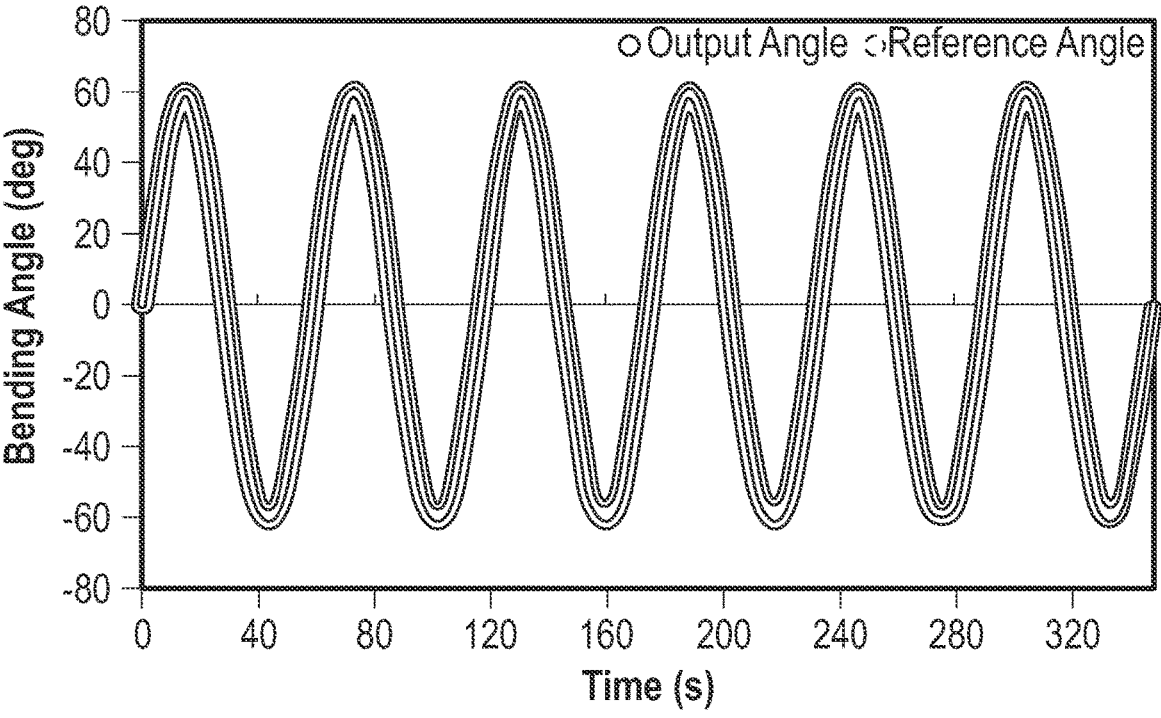
FIG. 11A provides overlaid plots of bending versus time for a reference (desired) angle and output angle obtained with a steerable surgical tubular needle and closed-loop PID control scheme as disclosed herein.

FIG. 11A provides overlaid plots of bending versus time for a reference (desired) angle and output angle obtained with a steerable surgical tubular needle and closed-loop PID control scheme as disclosed herein. FIG. 11A was implemented in Simulink (The Mathworks Inc.) to tune the PID coefficients. The controller's capability to match the output angle to the reference (desired) angle was evaluated when the reference bending angle changes between −30° to +30°. The simulation tuned the PID coefficients as P: 1.2, 1:5, and D: 0.02. FIG. 11A shows that output angle follows the reference angle.

Figure 11B:
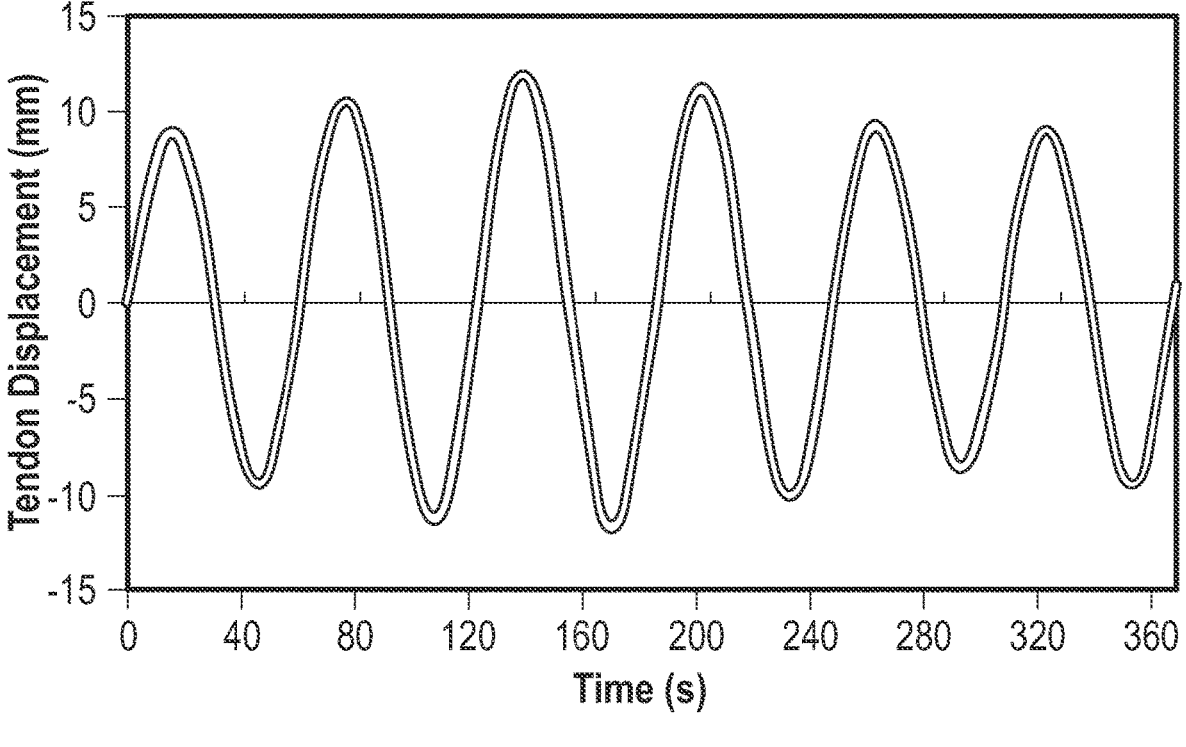
FIG. 11B is a plot of tendon displacement versus time obtained with a steerable surgical tubular needle and closed-loop PID control scheme as disclosed herein.

FIG. 11B is a plot of tendon displacement versus time obtained with a steerable surgical tubular needle and closed-loop PID control scheme as disclosed herein. Experimental tuning was performed when implementing the closed-loop control on an active steerable surgical tubular needle, by observing the effects of each coefficient on the overall system performance. The proportional gain affects the speed of reaching the desired angle, the integral gain reduces the steady state error, and the derivative gain reduces the overshoots. The experimentally tuned PID coefficients are P: 0.45, 1:0.0075, and D: 0.5. The system oscillates between two close values (with ±2° error from the desired angle).

Figure 12A:
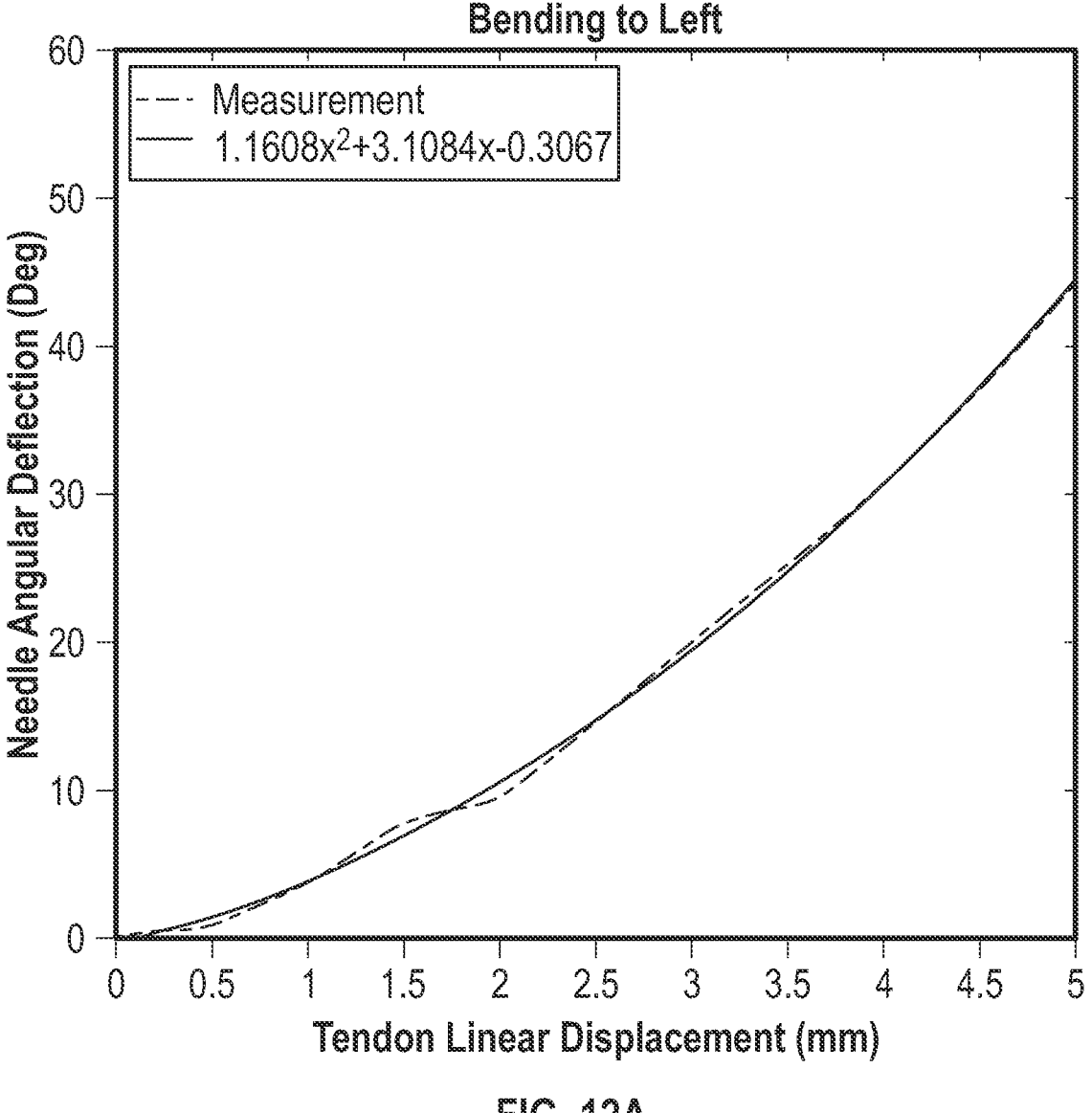
FIG. 12A provides overlaid plots of measured and modeled needle angle deflection versus tendon linear displacement for bending to the left of a steerable surgical tubular needle as disclosed herein.
Figure 12B:
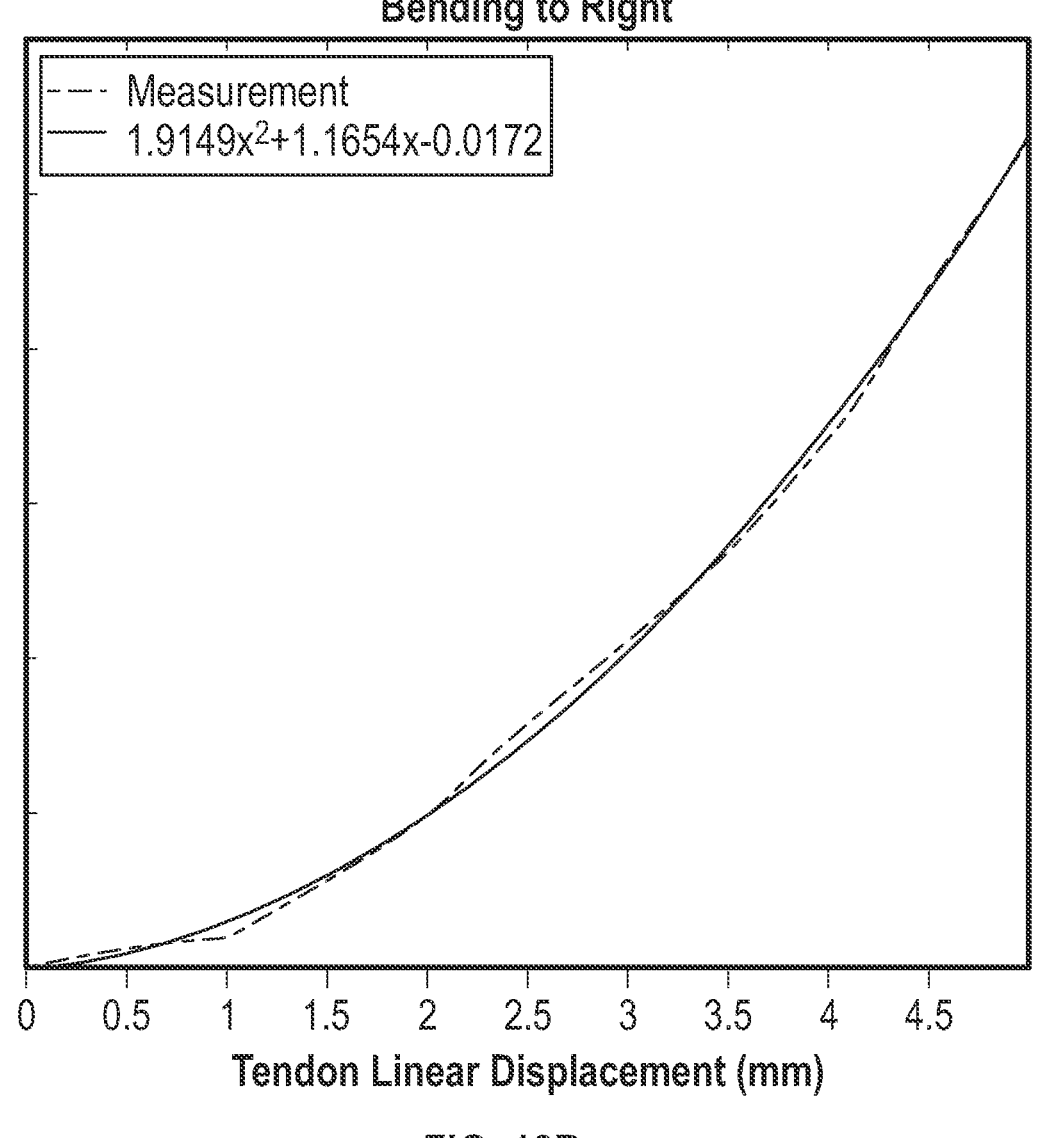
FIG. 12B provides overlaid plots of measured and modeled needle angle deflection versus tendon linear displacement for bending to the right of a steerable surgical tubular needle as disclosed herein.

Bending experiments were performed with the active needle and the actuation system to evaluate the controller. For each experiment, multiple bending angles were selected and provided as an input to the Python script. To characterize the flexure section, the tendons were linearly and independently displaced at increments of 0.5 mm. Images were taken of the flexure section at each increment and the angular deflection was measured using ImageJ. Once the maximum bending angle is reached, the actuators are stopped to prevent plastic deformation or fractures within the needle. Each trial starts with tensioning the tendons so that the hysteresis effect from the nitinol tendons is neglected. It is reasonable to assume that since the left side is mirrored from the right, the relationship will be very similar. A second order polynomial function was fitted to the data to model the relationship between the tendon displacement and the angular deflection of the flexure section. FIGS. 12A and 12B show the relationship between the tendon displacement and needle bending to the left and right, respectively. This relationship was used by the controller to make decisions on tendon displacement actions.

Figure 13:
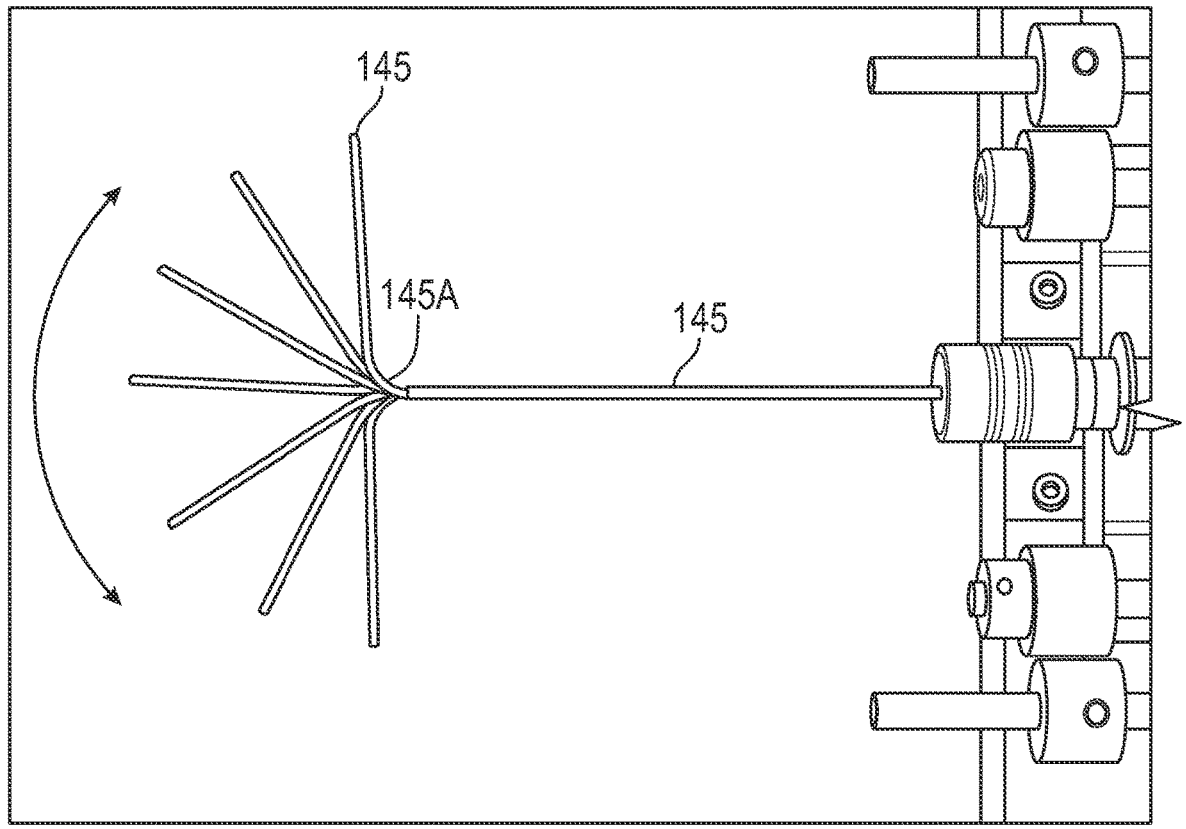
FIG. 13 shows a tendon-actuated steerable surgical needle according to certain embodiments of the present disclosure arranged in seven different positions spanning an angular range of 180 degrees.

To evaluate the efficacy of the piezoelectric actuators and the controller to realize a desired bending angle at the needle tip, needle manipulation experiments were performed using tendon displacement actuation and EM tracking position feedback. Only the modular needle manipulator (the top section of the robot) is used in this study. A 3D Guidance Model 55 electromagnetic (EM) tracking sensor (Northern Digital Inc., Waterloo, Canada) was installed on the needle tip (inside the needle tube) for accurate characterization of needle tip pose (position and orientation) with respect to its neutral axis. The EM sensors detect translational and rotational changes in pose. For the purpose of needle bending, the deflection angle could be measured directly using the yaw measurement from the EM sensor. The yaw was set to zero at the neutral axis of the needle. The pose data was recorded in real-time to a text file using CUBES program (Northern Digital Inc., Waterloo, Canada). The data, in predetermined time intervals, was imported to a Python script which uses the PID controller (described hereinabove) to determine the necessary displacement of each tendon to reach a desired bending angle. The control output values, calculated by the PID controller, were generated in pairs, float values of the same magnitude but opposite sign, to ensure that one tendon loosens while the other tightens during actuation. Various bending angles spanning 180 degrees were demonstrated, as provided in FIG. 13 (showing a tendon-actuated steerable surgical needle according to certain embodiments of the present disclosure arranged in seven different positions spanning an angular range of 180 degrees). The control output values were sent to their respective Arduino boards, at which point the values were processed and turned into a high/low voltage signal to turn the actuator and produce a desired displacement. The time and pose data during actuation were recorded via the same Python script in a separate text file for recordkeeping purposes. The script allows for multiple targets to be used in succession, allowing for a series of movements to be executed and recorded. Two shape functions served as the control input bending angle targets: (i) sine and (ii) triangle. The data recorded from the function trials was analyzed graphically to determine the efficacy of the piezoelectric rotary actuators for tendon displacement.

Figures 14A, 14B:
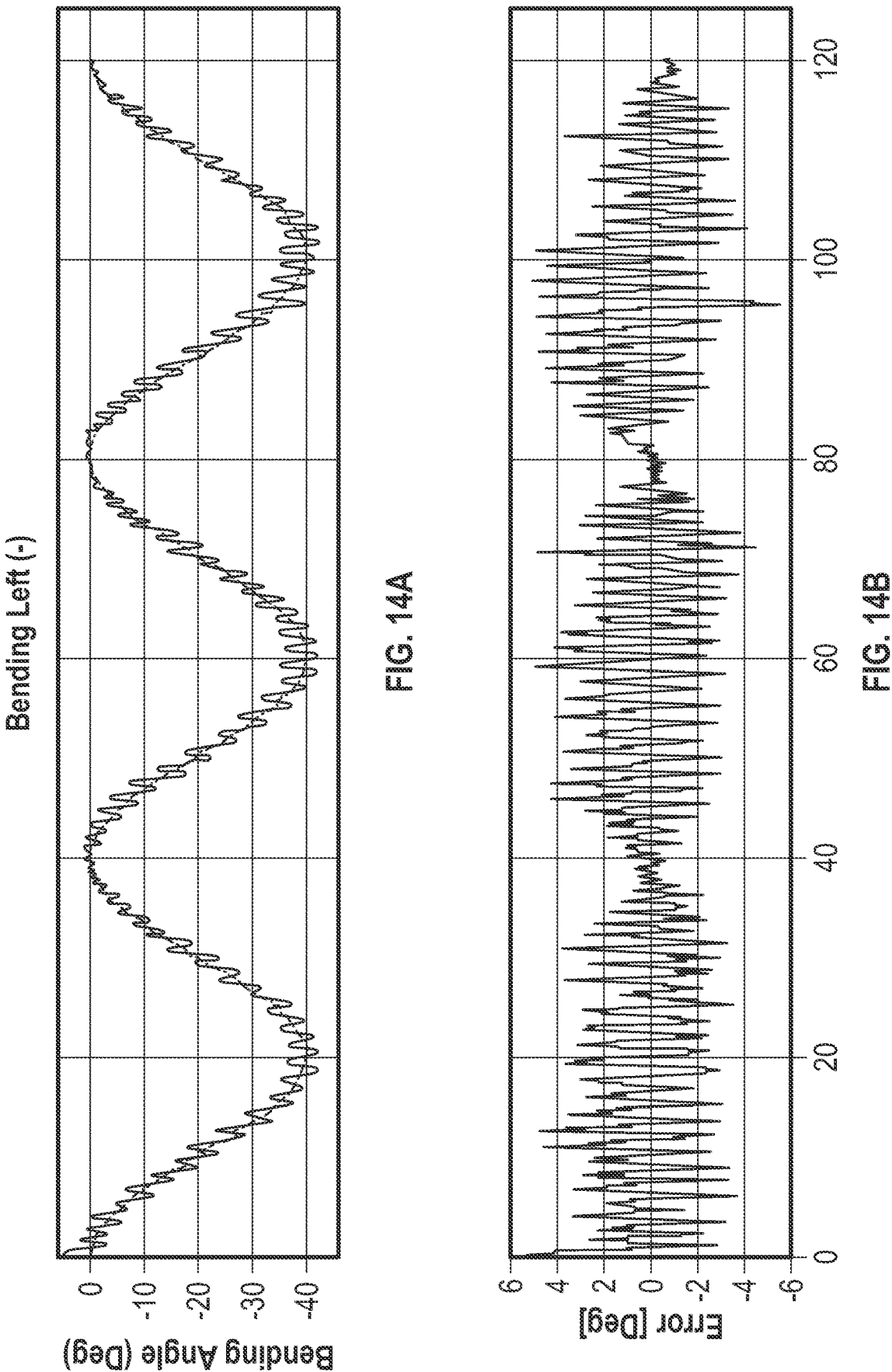
FIG. 14A is a plot of bending angle for bending to the left of a steerable surgical tubular needle as disclosed herein when actuated via piezoelectric tendon displacement actuation with a sine wave input signal.
FIG. 14B is a plot of tracking error obtained by electromagnetic tracking feedback for the needle bending characterized in FIG. 14A.
Figures 14C, 14D:
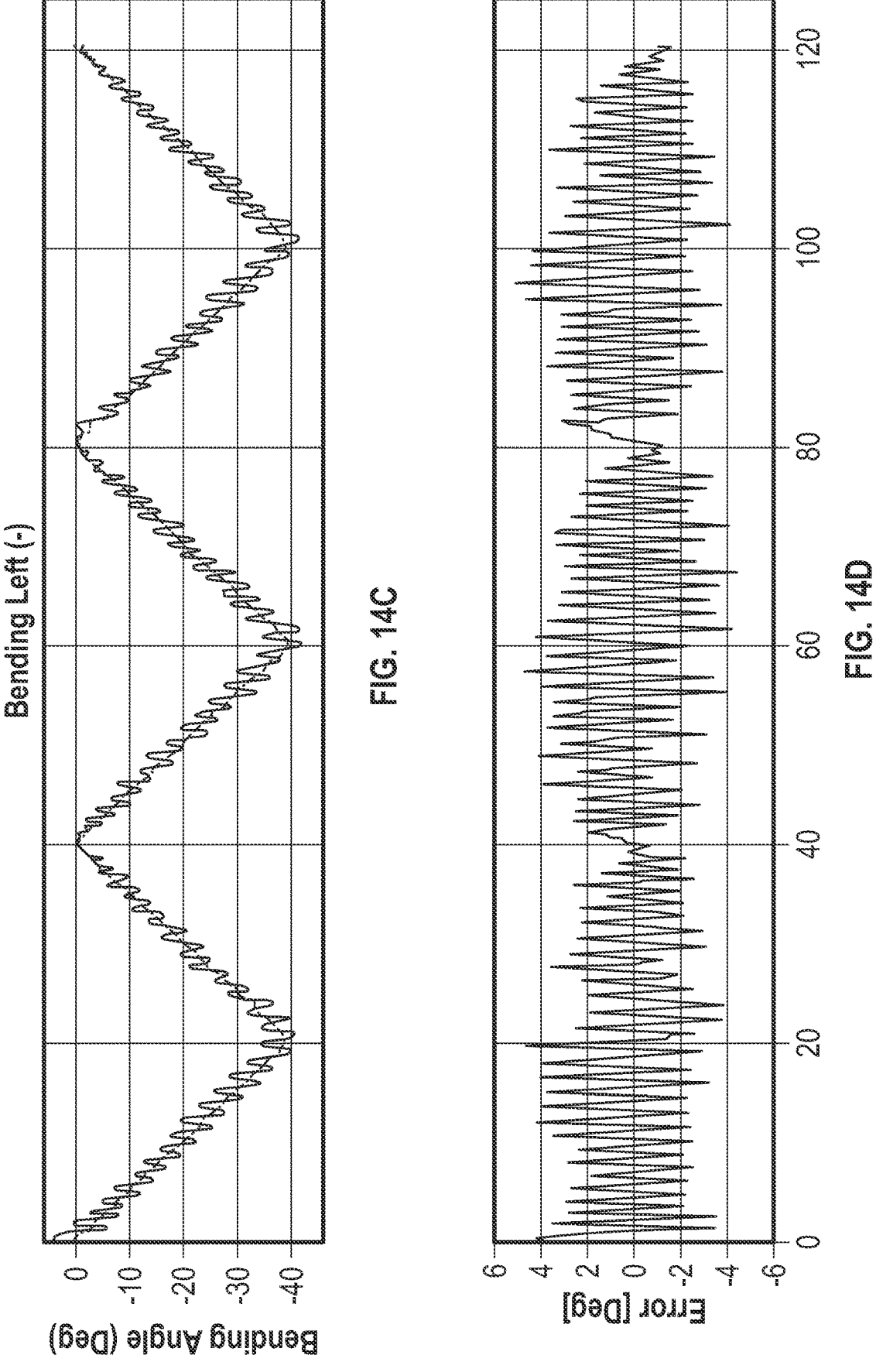
FIG. 14C is a plot of bending angle for bending to the left of a steerable surgical tubular needle as disclosed herein when actuated via piezoelectric tendon displacement actuation with a triangular wave input signal.
FIG. 14D is a plot of tracking error obtained by electromagnetic tracking feedback for the needle bending characterized in FIG. 14C.
Figures 15A, 15B:
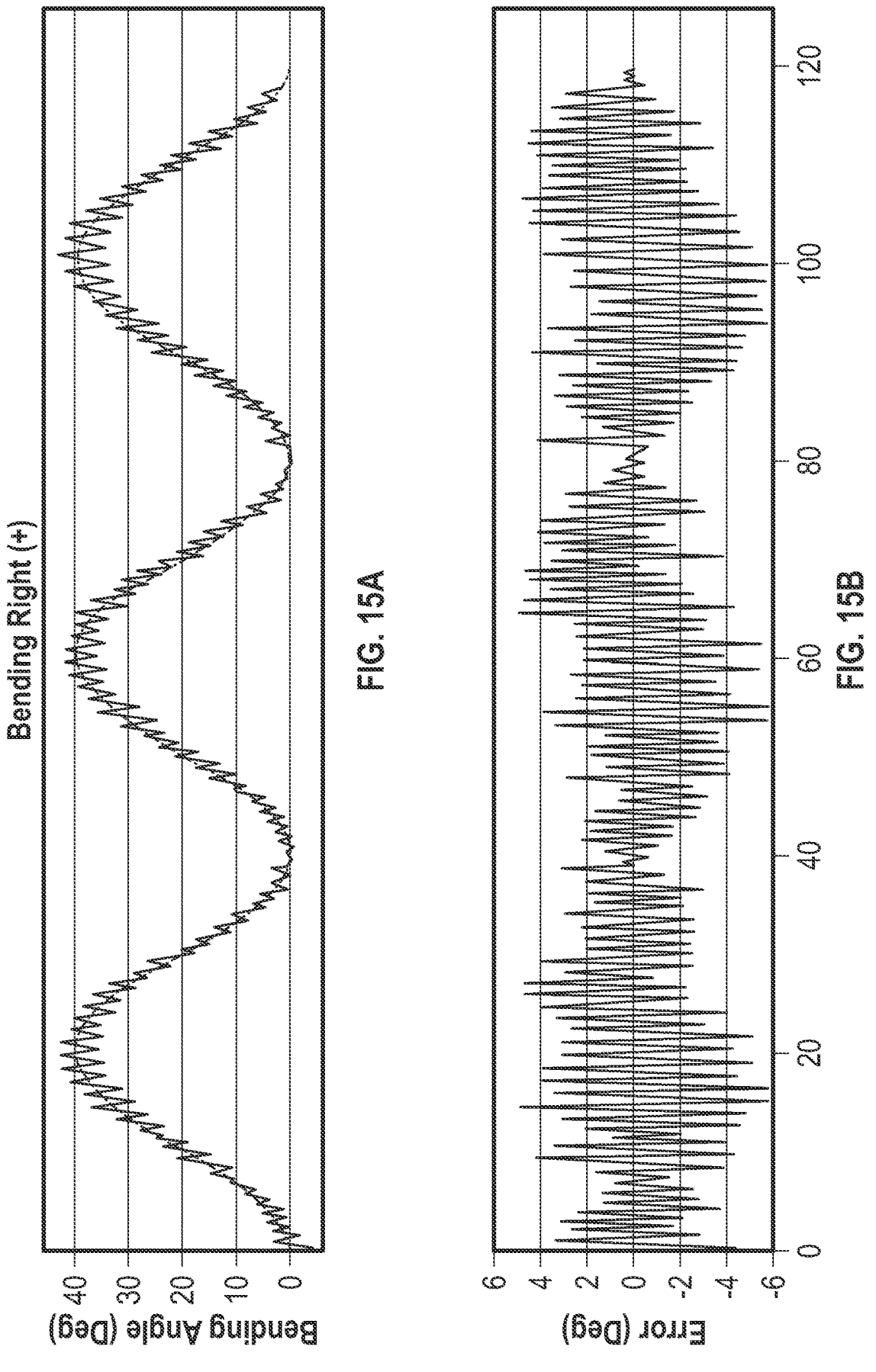
FIG. 15A is a plot of bending angle for bending to the right of a steerable surgical tubular needle as disclosed herein when actuated via piezoelectric tendon displacement actuation with a sine wave input signal.
FIG. 15B is a plot of tracking error obtained by electromagnetic tracking feedback for the needle bending characterized in FIG. 15A.
Figures 15C, 15D:
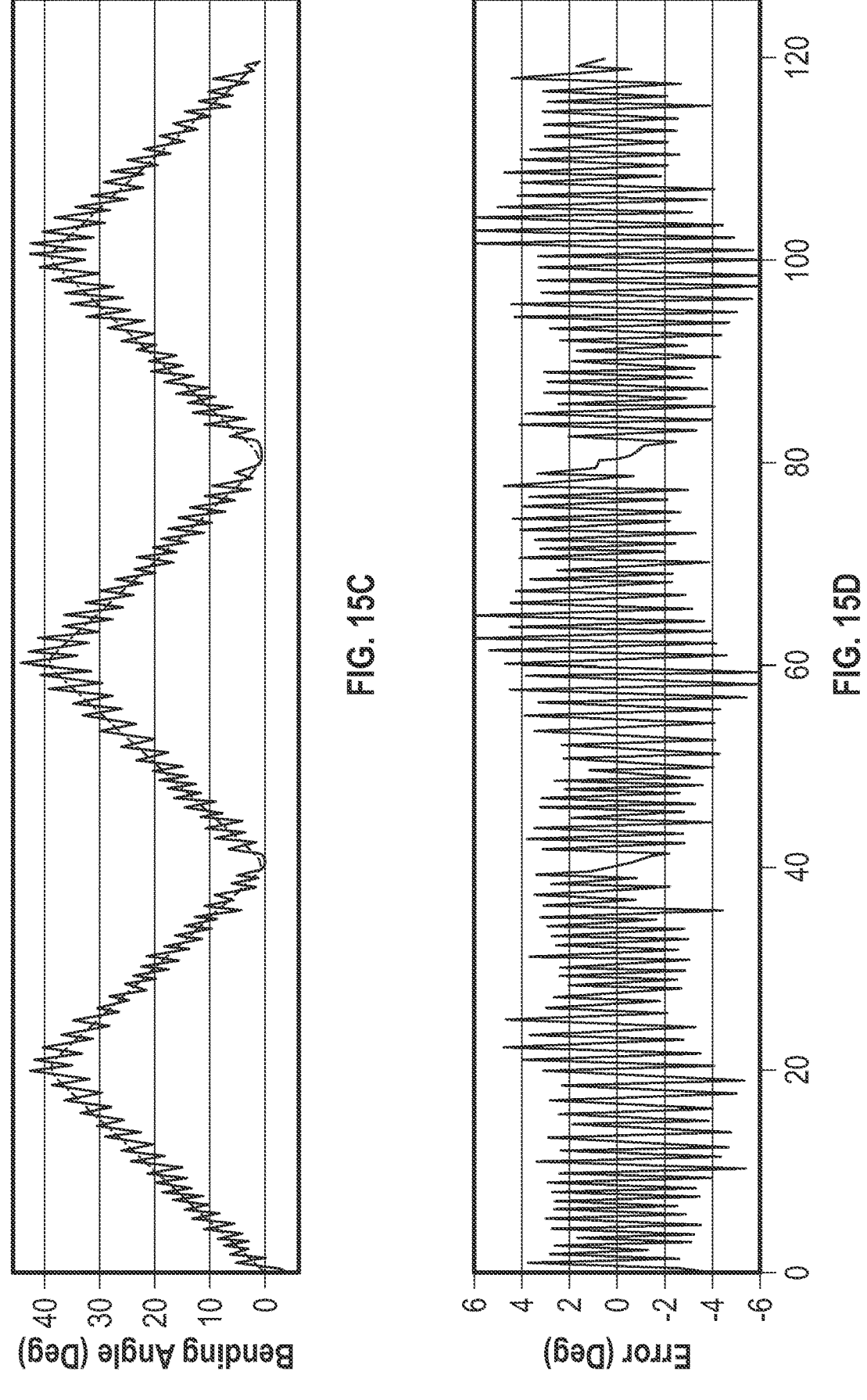
FIG. 15C is a plot of bending angle for bending to the right of a steerable surgical tubular needle as disclosed herein when actuated via piezoelectric tendon displacement actuation with a triangular wave input signal.
FIG. 15D is a plot of tracking error obtained by electromagnetic tracking feedback for the needle bending characterized in FIG. 15C.

FIGS. 14A to 15D show the PID controlled response of the active needle tip to follow desired positions (bending angles) via tendon displacement control and EM tracking feedback. FIG. 14A is a plot of bending angle to the left of a steerable surgical tubular needle when actuated via piezo-electric tendon displacement actuation with a sine wave input signal, and FIG. 14B is a plot of tracking error for the needle bending in FIG. 14B. FIG. 14C is a plot of bending angle to the left of a steerable surgical tubular needle when actuated via piezoelectric tendon displacement actuation with a triangular wave input signal, and FIG. 14D is a plot of tracking error for the needle bending in FIG. 14B. FIGS. 15A to 15D embody the same plots as the corresponding FIGS. 14A to 14D, but for needle bending to the right. Both the sine and triangle inputs exhibited little time delays. Due to the tuning of the controller, there was oscillation of the measured angle over and under the target angle. The average oscillation absolute error for the sine trials was 1.71 and 1.84 degrees towards left and right, respectively; and for triangle trials was 1.75 and 2.00 degrees towards left and right, respectively. The maximum absolute errors for each trial were 5.62, 6.66, 5.36, and 6.41 in the same order. The average (non-absolute) errors for the sinewave trials were 0.28 and −0.27 degrees towards left and right, respectively; and similarly for the triangle wave were 0.28 and −0.24 degrees towards left and right, respectively. The average oscillation absolute error of tracking a desired bending angle towards left and right (combined) for the sine and triangle waves was 1.78 and 1.88 degrees, respectively. By observing the non-absolute mean errors, which effectively nullify the effects of oscillation, it is concluded that the controller is capable of effectively manipulating the needle to follow a defined trajectory with less than 0.30 degrees error. With more accurate experimental tuning, the controller can dampen the oscillation significantly and realize the aforementioned accuracy.

Figure 16A:
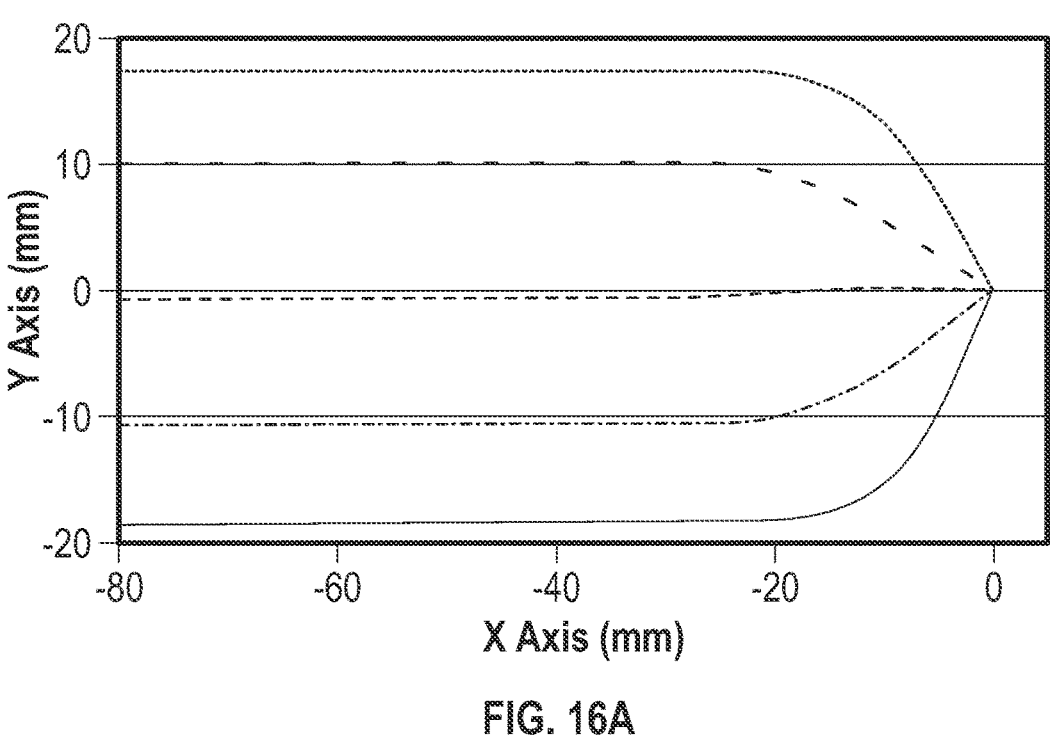
FIG. 16A provides five (5) simulated trajectory plots (y axis versus x axis displacement) to reach the same target point, achieved by applying different bending angles using a modeled steerable surgical tubular needle according to a design as disclosed herein.
Figure 16B:
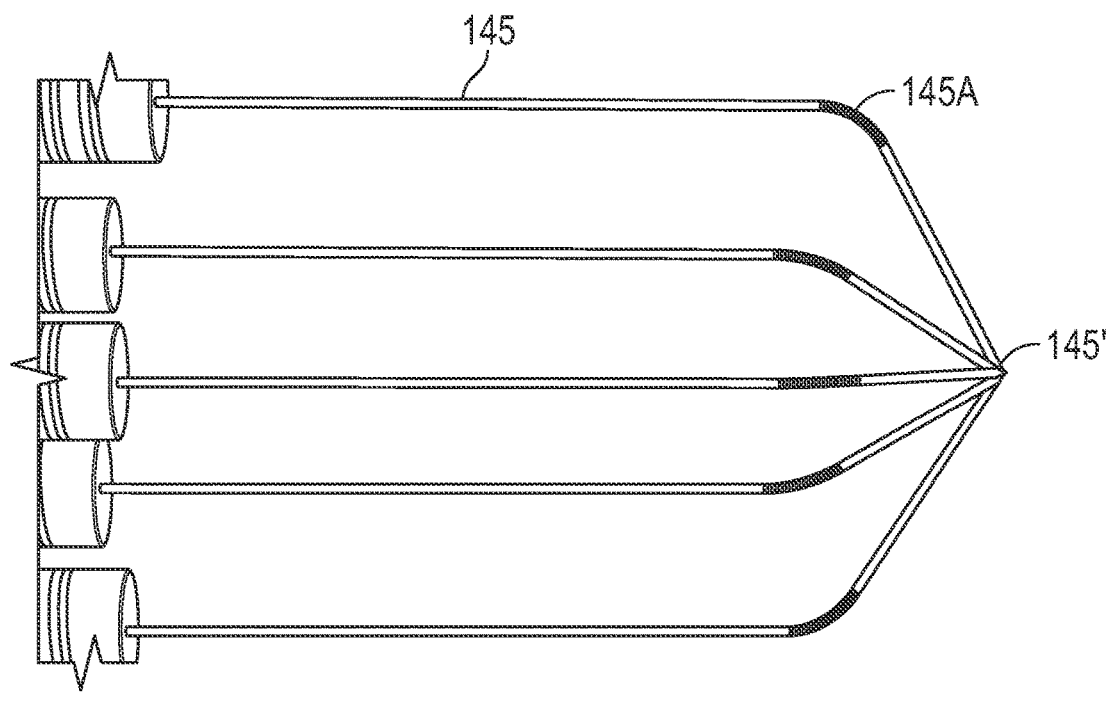
FIG. 16B provides five redrawn overlaid images of actual steerable surgical tubular needle trajectories to reach the same target point, using a steerable surgical tubular needle and apparatus as disclosed herein.

FIG. 16A shows the capability of the system in trajectory tracking, where five simulated trajectories were followed to place the needle tip at a desired target position, achieved by applying different bending angles using a modeled steerable surgical tubular needle according to a design as disclosed herein. The steerable surgical apparatus was commanded to reach the target position via five solved solutions, and their trajectories were recorded. Such trajectories are overlaid in FIG. 16B to visually illustrate this kinematic. The five solved trajectories (the same target position from multiple approach paths) of FIG. 16A and the actual trajectories of FIG. 16B were compared to estimate the accuracy. The experiments demonstrated root mean square error (RMSE) of 0.86 mm, and standard deviation of 0.36 mm.

Figure 17:
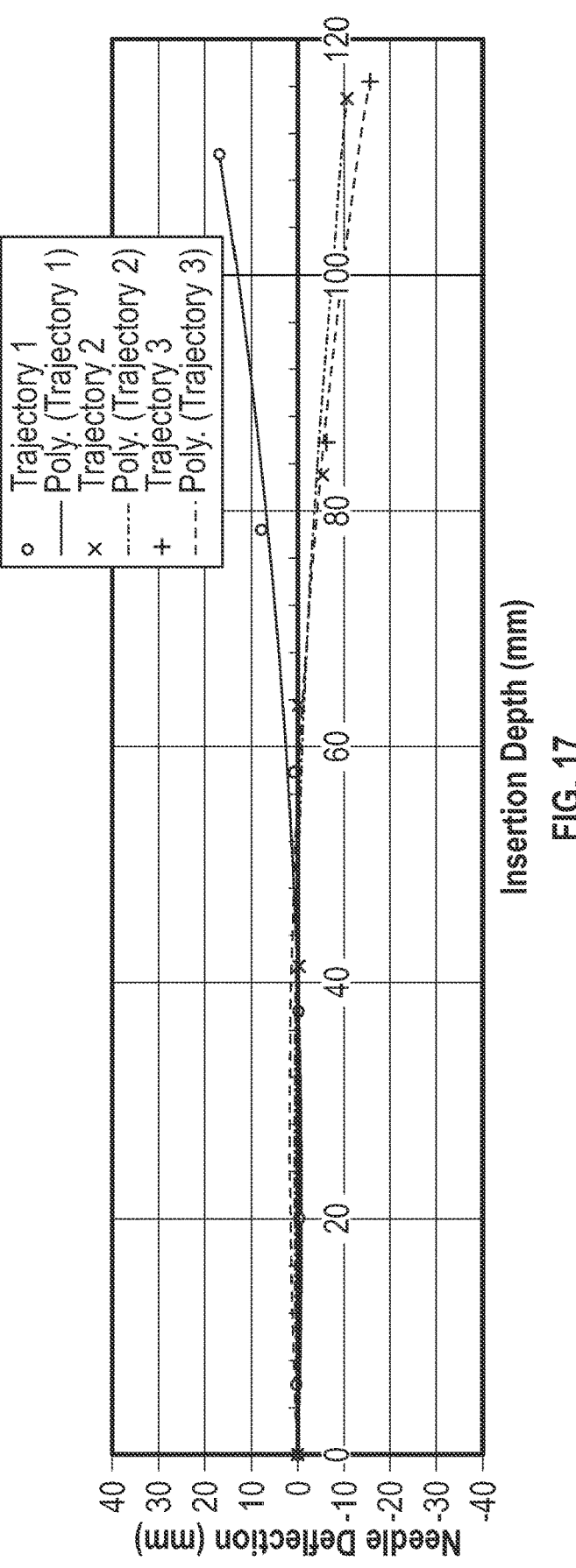
FIG. 17 provides plots of needle deflection versus insertion depth for three trajectories of a steerable surgical tubular needle inserted into a phantom tissue.

FIG. 17 provides plots of needle deflection versus insertion depth for three trajectories of a steerable surgical tubular needle inserted into a phantom tissue.

The terminology used herein is for the purpose of describing particular aspects only and is not intended to be limiting of the disclosure. As used herein, the singular forms "a," "an," and "the" are intended to include the plural forms as well, unless the context clearly indicates otherwise. As used herein, the term "and/or" includes any and all combinations of one or more of the associated listed items. It will be further understood that the terms "comprises," "comprising," "includes," and/or "including" when used herein specify the presence of stated features, integers, actions, steps, operations, elements, and/or components, but do not preclude the presence or addition of one or more other features, integers, actions, steps, operations, elements, components, and/or groups thereof.

As used herein, the term "patient" means an animal, preferably a mammal, and most preferably a human.

A "control unit" or "controller" as disclosed herein may utilize a computer processor and be adapted to execute instructions from a computer-readable medium to perform any of the functions or processing described herein. A control unit or controller may be a circuit or circuits included in an electronic board or card, such as a printed circuit board (PCB), a server, a personal computer, a desktop computer, a laptop computer, a personal digital assistant (PDA), a computing pad, a mobile device, or any other device, and may represent, for example, a server or a user's computer. A control unit or controller may include a memory and one or more general-purpose processing devices, such as a microprocessor, central processing unit (CPU), or the like; complex instruction set computing (CISC) microprocessor, a reduced instruction set computing (RISC) microprocessor, a very long instruction word (VLIW) microprocessor, a processor implementing other instruction sets, or other processors implementing a combination of instruction sets.

It will be understood that, although the terms first, second, etc., may be used herein to describe various elements, these elements should not be limited by these terms. These terms are only used to distinguish one element from another. For example, a first element could be termed a second element, and, similarly, a second element could be termed a first element without departing from the scope of the present disclosure.

It will be understood that when an element is referred to as being "connected" or "coupled" to another element, it can be directly connected or coupled to the other element, or intervening elements may be present. In contrast, when an element is referred to as being "directly connected" or "directly coupled" to another element, there are no intervening elements present.

Unless otherwise defined, all terms (including technical and scientific terms) used herein have the same meaning as commonly understood by one of ordinary skill in the art to which this disclosure belongs. It will be further understood that terms used herein should be interpreted as having a meaning consistent with their meaning in the context of this specification and the relevant art and will not be interpreted in an idealized or overly formal sense unless expressly so defined herein.

It is to be understood that the present disclosure is not limited to the aspects described above and illustrated in the drawings; rather, the skilled person will recognize that many changes and modifications may be made within the scope of the present disclosure and appended claims. In the drawings and specification, there have been disclosed aspects for purposes of illustration only and not for purposes of limitation, the scope of the disclosure being set forth in the following claims.

REFERENCES

[1] Philips, "Philips DynaTRIM Targeted Trans-Rectal Interventional MRI" [Online]. Available: https://www.philips.co.in/healthcare/product/HC784008/dynatrim-targeted-trans-rectal-interventional-mri.

[2] Kasivisvanathan, V., Stabile, A., Neves, J. B., Giganti, F., Valerio, M., Shanmugabavan, Y., Clement, K. D., Sarkar, D., Philippou, Y., Thurtle, D., Deeks, J., Emberton, M., Takwoingi, Y., and Moore, C. M., 2019, "Magnetic Resonance Imaging-Targeted Biopsy Versus Systematic Biopsy in the Detection of Prostate Cancer: A Systematic Review and Meta-Analysis," Eur. Urol., 76 (3), pp. 284-303.

[3] van der Leest, M., Cornel, E., Israël, B., Hendriks, R., Padhani, A. R., Hoogenboom, M., Zamecnik, P., Bakker, D., Setiasti, A. Y., Veltman, J., van den Hout, H., van der Lelij, H., van Oort, I., Klaver, S., Debruyne, F., Sedelaar, M., Hannink, G., Rovers, M., Hulsbergen-van de Kaa, C., and Barentsz, J. O., 2019, "Head-to-Head Comparison of Transrectal Ultrasound-Guided Prostate Biopsy Versus Multiparametric Prostate Resonance Imaging with Subsequent Magnetic Resonance-Guided Biopsy in Biopsy-Naïve Men with Elevated Prostate-Specific Antigen: A Large Prospective Mu," Eur. Urol., 75 (4), pp. 570-578.

[4] Ahdoot, M., Wilbur, A. R., Reese, S. E., Lebastchi, A. H., Mehralivand, S., Gomella, P. T., Bloom, J., Gurram, S., Siddiqui, M., Pinsky, P., Parnes, H., Linehan, W. M., Merino, M., Choyke, P. L., Shih, J. H., Turkbey, B., Wood, B. J., and Pinto, P. A., 2020, "MRI-Targeted, Systematic, and Combined Biopsy for Prostate Cancer Diagnosis," N. Engl. J. Med., 382 (10), pp. 917-928.

[5] Perrin, A., Venderink, W., Patak, M. A., Möckel, C., Fehr, J. L., Jichlinski, P., Porcellini, B., Lucca, I., Futterer, J., and Valerio, M., 2021, "The Utility of In-Bore Multiparametric Magnetic Resonance-Guided Biopsy in Men with Negative Multiparametric Magnetic Resonance-Ultrasound Software-Based Fusion Targeted Biopsy," Urol. Oncol. Semin. Orig. Investig., 39 (5), pp. 297.e9-297.e16.

[6] Meermeier, N. P., Foster, B. R., Liu, J. J., Amling, C. L., and Coakley, F. V., 2019, "Impact of Direct MRI-Guided Biopsy of the Prostate on Clinical Management," Am. J. Roentgenol., 213 (2), pp. 371-376.

[7] Addicott, B., Foster, B. R., Johnson, C., Fung, A., Amling, C. L., and Coakley, F. V., 2017, "Direct Magnetic Resonance Imaging-Guided Biopsy of the Prostate: Lessons Learned in Establishing a Regional Referral Center," Transl. Androl. Urol., 6 (3), pp. 395-405.

What is claimed is:

1. A steerable surgical apparatus comprising:

a steerable surgical tubular needle comprising first and second tendons extending through an interior of the steerable surgical tubular needle;

a needle manipulation apparatus configured to manipulate the steerable surgical tubular needle, the needle manipulation apparatus comprising a plurality of controllable actuators configured to permit adjustment of needle rotation, needle translation, and needle bending, wherein the needle manipulation apparatus is devoid of ferrous materials, wherein the plurality of controllable actuators comprises a first nonmagnetic piezoelectric actuator configured to selectively apply tension to the first tendon for bending a tip portion of the needle in a first direction, and comprises a second nonmagnetic piezoelectric actuator configured to selectively apply tension to the second tendon for bending the tip portion in a second direction, and the needle manipulation apparatus is configured to be placed and operated within a magnetic resonance imaging machine bore;

a plurality of fiducial markers affixed to the needle manipulation apparatus;

a plurality of encoders configured to sense movements initiated by the plurality of actuators, wherein the plurality of encoders comprises a first linear encoder having an associated first linear encoder controller configured to detect position of the first tendon, and comprises a second linear encoder having an associated second linear encoder controller configured to detect position of the second tendon; and a control unit configured to (i) utilize positional information derived from imaging the plurality of fiducial markers to establish position and orientation of the needle manipulation apparatus within the magnetic resonance imaging machine bore, and (ii) utilize signals obtained from the plurality of encoders to determine position and orientation of the steerable surgical tubular needle, including bending of the steerable surgical needle by tension applied to the first tendon by the first nonmagnetic piezoelectric actuator and applied to the second tendon by the second nonmagnetic piezoelectric actuator, when the steerable surgical needle is inserted into a body of a patient within the magnetic resonance imaging machine bore.

2. The steerable surgical apparatus of claim 1, wherein the control unit is further configured to control operation of the plurality of controllable actuators to effectuate the adjustment of needle rotation, needle translation, and needle bending when the needle is inserted into the patient within the magnetic resonance imaging machine bore.

3. The steerable surgical apparatus of claim 1, wherein the plurality of controllable actuators comprises nonmagnetic piezoelectric actuators.

4. The steerable surgical apparatus of claim 1, wherein the control unit is configured to apply kinematic functions in combination with the signals obtained from the plurality of encoders to determine the position and orientation of the steerable surgical tubular needle when inserted into a patient within the magnetic resonance imaging machine bore.

5. The steerable surgical apparatus of claim 1, wherein the steerable surgical tubular needle comprises multiple groups of transverse notches defined in a wall of the tubular needle, wherein each group of transverse notches of the multiple groups of transverse notches extends in a different direction relative to each other group of transverse notches.

6. The steerable surgical apparatus of claim 5, further comprising a tray member actuator configured to manipulate the guidewire to translate the moveable tray member in the longitudinal direction.

7. The steerable surgical apparatus of claim 1, wherein the steerable surgical tubular needle comprises:

a tubular body having a distal end;

a longitudinal passage extending in a longitudinal direction within an interior of the steerable surgical tubular needle;

a moveable tray member arranged at the distal end of the tubular body and coupled to a longitudinal guidewire, the moveable tray member comprising at least one lateral opening in communication with the longitudinal passage, and being configured to translate in the longitudinal direction between an extended position and a retracted position; and a retractable tip member positionable at a distal end of the moveable tray member.

8. The steerable surgical apparatus of claim 1, further comprising a fiducial frame containing the plurality of fiducial markers, wherein multiple fiducial markers of the plurality of fiducial markers are supported by the fiducial frame to be positioned in different respective planes, wherein each fiducial marker of the plurality of fiducial markers contains MRI-visible high contrast fluid.

9. The steerable surgical apparatus of claim 1, wherein the plurality of controllable actuators comprises a third actuator configured to permit the adjustment of needle translation, and the control unit is configured to control operation of the third actuator.

10. The steerable surgical apparatus of claim 1, wherein the plurality of controllable actuators comprises a fourth actuator configured to permit the adjustment of needle rotation, and the control unit is configured to control operation of the fourth actuator.

11. The steerable surgical apparatus of claim 1, further comprising at least one translation mechanism configured to permit the translation of the needle manipulation apparatus along at least one axis, and at least one translation mechanism actuator to control translation of the needle manipulation apparatus along the at least one axis.

12. The steerable surgical apparatus of claim 11, wherein the at least one axis comprises a plurality of orthogonal axes.

13. The steerable surgical apparatus of claim 11, wherein the control unit is configured to control operation of the at least one translation mechanism actuator.

14. The steerable surgical apparatus of claim 11, wherein the at least one translation mechanism comprises at least one Scott-Russell mechanism.

15. A method for performing a surgical procedure utilizing the steerable surgical apparatus of claim 1 in conjunction with a magnetic resonance imaging device having the magnetic resonance imaging machine bore, the method comprising:

inserting the steerable surgical tubular needle into the body of the patient; and while the patient and the needle manipulation apparatus are present within the magnetic resonance imaging bore:

(a) supplying the positional information derived from imaging of the fiducial markers to the control unit, and utilizing, by the control unit, the positional information to establish the position and orientation of the needle manipulation apparatus;

(b) utilizing, by the control unit, the signals obtained from the plurality of encoders to determine the position and orientation of the steerable surgical tubular needle within the body of the patient; and (c) controlling, by the control unit, the plurality of controllable actuators to adjust the needle rotation, needle translation, and needle bending of the steerable surgical tubular needle and thereby control movement of the steerable surgical tubular needle within the body of the patient.

16. The method of claim 15, wherein:

the controlling, by the control unit, of the plurality of controllable actuators comprises controlling the first nonmagnetic piezoelectric actuator to selectively apply tension to the first tendon for bending the tip portion in the first direction, and comprises controlling the second nonmagnetic piezoelectric actuator to selectively apply tension to the second tendon for bending the tip portion in the second direction.

17. The method of claim 15, wherein:

the steerable surgical tubular needle comprises:

a tubular body having a distal end;

a longitudinal passage extending in a longitudinal direction within an interior of the steerable surgical tubular needle;

a moveable tray member arranged at the distal end of the tubular body and coupled to a longitudinal guidewire, the moveable tray member comprising at least one lateral opening in communication with the longitudinal passage, and being configured to translate in the longitudinal direction between an extended position and a retracted position; and a retractable tip member positionable at a distal end of the moveable tray member; and the method further comprises controlling, by the control unit, a tray member actuator coupled with the guidewire to translate the moveable tray member through the longitudinal passage.

18. The method of claim 17, further comprising receiving a tissue sample from the patient through the at least one lateral opening into the moveable tray member, and removing the tissue sample by translating the moveable tray member through the longitudinal passage.

19. The method of claim 15, further comprising:

receiving image data from the magnetic resonance imaging device; and responsive to the receipt of the image data, controlling, by the control unit, the plurality of controllable actuators to adjust the needle rotation, needle translation, and needle bending of the steerable surgical tubular needle and thereby control the movement of the steerable surgical tubular needle within the body of the patient.

20. The method of claim 15, wherein the surgical procedure comprises brachytherapy, and the method further comprises delivering at least one radioactive material through the steerable surgical needle to one or more locations within the body of the patient.

* * * * *